US012570974B2

(12) United States Patent
Sobue et al.

(10) Patent No.: US 12,570,974 B2
(45) Date of Patent: Mar. 10, 2026

(54) OLIGONUCLEOTIDES FOR CONTROLLING TAU SPLICING, AND USES THEREOF

(71) Applicants: AICHI MEDICAL UNIVERSITY, Nagakute (JP); KNC LABORATORIES CO., LTD., Kobe (JP); NATIONAL UNIVERSITY CORPORATION SHIGA UNIVERSITY OF MEDICAL SCIENCE, Otsu (JP)

(72) Inventors: Gen Sobue, Aichi (JP); Kentaro Sahashi, Aichi (JP); Shinsuke Ishigaki, Aichi (JP); Kuniyuki Endo, Aichi (JP); Tsuyoshi Fujihara, Hyogo (JP); Masahiro Neya, Hyogo (JP); Seiji Matsuda, Hyogo (JP)

(73) Assignees: KNC LABORATORIES CO., LTD., Kobe (JP); AICHI MEDICAL UNIVERSITY, Nagakute (JP); NATIONAL UNIVERSITY CORPORATION SHIGA UNIVERSITY OF MEDICAL SCIENCE, Otsu (JP)

(*) Notice: Subject to any disclaimer, the term of this patent is extended or adjusted under 35 U.S.C. 154(b) by 32 days.

(21) Appl. No.: 17/257,412

(22) PCT Filed: Jul. 3, 2019

(86) PCT No.: PCT/JP2019/026470

§ 371 (c)(1),
(2) Date: Dec. 31, 2020

(87) PCT Pub. No.: WO2020/009151

PCT Pub. Date: Jan. 9, 2020

(65) Prior Publication Data

US 2021/0230598 A1 Jul. 29, 2021

(30) Foreign Application Priority Data

Jul. 4, 2018 (JP) ................................ 2018-127872

(51) Int. Cl.
*C12N 15/113* (2010.01)
*A61P 25/28* (2006.01)

(52) U.S. Cl.
CPC ........... *C12N 15/113* (2013.01); *A61P 25/28* (2018.01); *C12N 2310/11* (2013.01);
(Continued)

(58) Field of Classification Search
CPC ............. C12N 15/113; C12N 2310/11; C12N 2310/315; C12N 2310/321;
(Continued)

(56) References Cited

U.S. PATENT DOCUMENTS 10,793,856 B2 * 10/2020 Kordasiewicz ......... A61P 25/00
2003/0170704 A1 9/2003 Stamm et al.
(Continued)

FOREIGN PATENT DOCUMENTS

CN 1721437 A 1/2006
CN 104602708 A 5/2015
(Continued)

OTHER PUBLICATIONS

Matsuzono et al. Antisense Oligonucleotides Reduce RNA Foci in Spinocerebellar Ataxia 36 Patient iPSCs, 2017, Molecular Therapy: Nucleic Acids, 8, p. 211-219 (Year: 2017).*
(Continued)

*Primary Examiner* — Jennifer Dunston
*Assistant Examiner* — Keyur A Vyas
(74) *Attorney, Agent, or Firm* — Sughrue Mion, PLLC

(57) ABSTRACT

The present invention provides a tau exon 10 skipping-promoting antisense oligonucleotide containing at least one
(Continued)

2'-O, 4'-C-ethylene-bridged nucleic acid, and a nucleotide sequence complementary to a sequence consisting of at least 10 continuous nucleotides in a region consisting of the nucleotide sequence shown in SEQ ID NO: 44 in exon 10 of a tau mRNA precursor. In addition, the present invention provides a tau exon 10 skipping-suppressing antisense oligonucleotide containing at least one 2'-O, 4'-C-ethylene-bridged nucleic acid, and a nucleotide sequence complementary to a sequence consisting of at least 10 continuous nucleotides in a region consisting of the nucleotide sequence shown in SEQ ID NO: 45 in intron 10 of a tau mRNA precursor.

5 Claims, 15 Drawing Sheets

Specification includes a Sequence Listing.

(52) U.S. Cl.
CPC .. *C12N 2310/315* (2013.01); *C12N 2310/321* (2013.01); *C12N 2310/3231* (2013.01)

(58) Field of Classification Search
CPC ...... C12N 2310/3231; C12N 2310/346; C12N 2320/33; A61P 25/28; A61P 43/00; A01K 2267/0312; A01K 2267/0318
See application file for complete search history.

(56) References Cited

U.S. PATENT DOCUMENTS

| | | | |
|---|---|---|---|
| 2008/0249058 A1 | 10/2008 | Roberson et al. | |
| 2014/0298496 A1 | 10/2014 | Krainer et al. | |
| 2015/0183854 A1 | 7/2015 | Mori et al. | |
| 2015/0275205 A1 | 10/2015 | Miller et al. | |
| 2016/0032285 A1* | 2/2016 | Rigo | A61P 25/00 435/375 |
| 2017/0211064 A1 | 7/2017 | Rigo | |
| 2018/0112217 A1* | 4/2018 | Hansen | C12N 15/117 |
| 2020/0148753 A1 | 5/2020 | Mori et al. | |
| 2022/0340646 A1 | 10/2022 | Mori et al. | |

FOREIGN PATENT DOCUMENTS

| | | |
|---|---|---|
| WO | 2014/153236 A1 | 9/2014 |
| WO | 2016/019063 A1 | 2/2016 |
| WO | 2018/066701 A1 | 4/2018 |

OTHER PUBLICATIONS

Magner et al. Influence of mismatched and bulged nucleotides on SNP-preferential RNase H cleavage of RNA-antisense gapmer heteroduplexes, 2017, Scientific Reports, 7, 12532, p. 1-16 (Year: 2017).*

Wan and Seth, The Medicinal Chemistry of Therapeutic Oligonucleotides, 2016, J. Med. Chem., 21, 9645-9667 (Year: 2016).*

Sazani et al., Splice Switching Oligonucleotides as Potential Therapeutics, 2008, Antisense Drug Technology: Principles, strategies and Applications, 2nd Ed. p. 89-114. (Year: 2008).*

Koizumi, 2-O,4-C-Ethylene-Bridged Nucleic Acids (ENATM) as Next-Generation Antisense and Antigene Agents, 2004, Biol. Pharm Bull., 27, 453-456. (Year: 2004).*

International Search Report, issued Oct. 1, 2019, in International Application No. PCT/JP2019/026470.

Ishigaki et al., "Altered Tau Isoform Ratio Caused by Loss of FUS and SFPQ Function Leads to FTLD-like Phenotypes", Cell Reports, 2017, vol. 18, pp. 1118-1131 (15 pages total).

Schoch et al., "Increased 4R-tau induces pathological changes in a human-tau mouse model", Neuron, 2016, vol. 90, No. 5, pp. 941-947 (15 pages total).

Sahashi et al., "Tsunami: an antisense method to phenocopy splicing-associated diseases in animals", Genes & Development, 2012, vol. 26, pp. 1874-1884 (12 pages total).

Sahashi et al., "Pathological impact of SMN2 mis-splicing in adult SMA mice", EMBO Molecular Medicine, 2013, vol. 5, pp. 1586-1601 (16 pages total).

Lisowiec et al., "Structural determinants for alternative splicing regulation of the MAPT pre-mRNA", RNA Biology, 2015, vol. 12, No. 3, pp. 330-342 (13 pages total).

Morita et al., "2'-O,4'-C-Ethylene-Bridged Nucleic Acids (ENA): Highly Nuclease-Resistant and Thermodynamically Stable Oligonucleotides for Antisense Drug", Bioorganic & Medicinal Chemistry Letters, 2002, vol. 12, pp. 73-76 (4 pages total).

Partial Supplementary European Search Report, dated May 13, 2022, issued by the European Patent Office in European Application No. 19830765.4.

* cited by examiner

4R/3R-tau ratio (RT-PCR)

4R/3R-tau ratio (cerebral cortex, RT-PCR)

4R/3R-tau ratio (hippocampus, RT-PCR)

4R/3R-tau ratio (cerebral cortex, RT-PCR)

4R/3R-tau protein ratio (hippocampus, Western blot)

4R/3R-tau ratio (cerebral cortex, RT-PCR)

4R/3R-tau ratio (hippocampus, RT-PCR)

4R/3R-tau ratio (hippocampus, RT-PCR)

4R/3R-tau ratio (cerebral cortex, RT-PCR)

Fig. 12-1
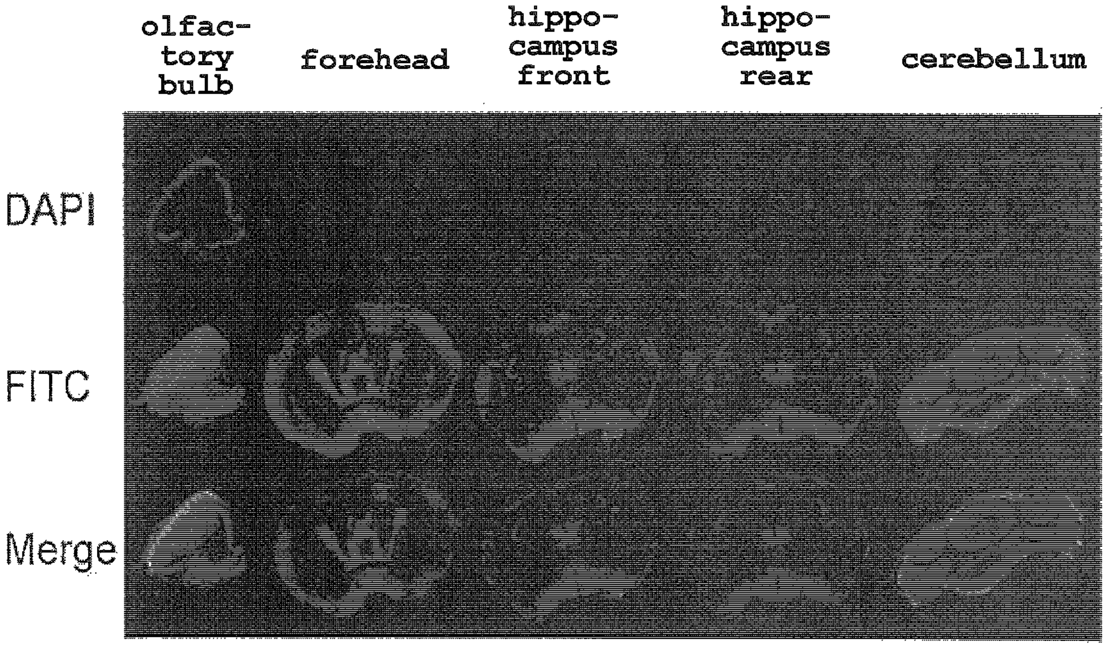
Fig. 12-2
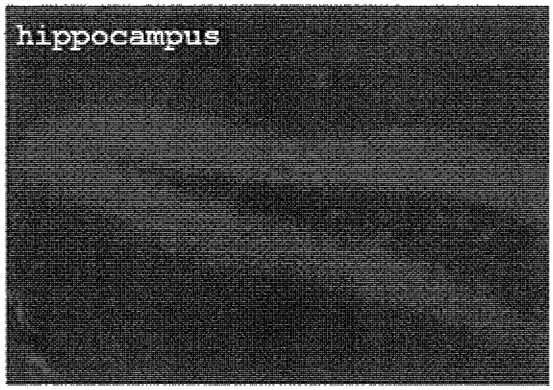
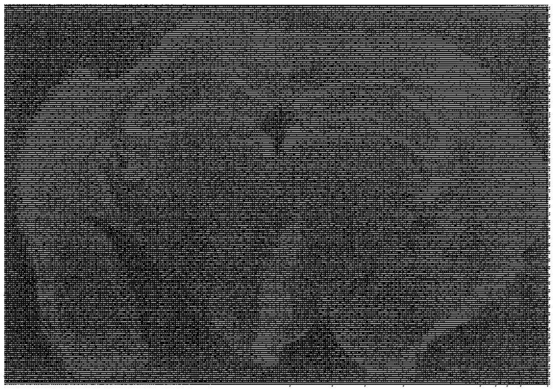

OLIGONUCLEOTIDES FOR CONTROLLING TAU SPLICING, AND USES THEREOF

CROSS REFERENCE TO RELATED APPLICATIONS

This application is a National Stage of International Application No. PCT/JP2019/026470, filed Jul. 3, 2019, claiming priority based on Japanese Patent Application No. 2018-127872, filed Jul. 4, 2018.

TECHNICAL FIELD

The present invention relates to an antisense oligonucleotide (hereinafter sometimes to be abbreviated as "ASO") that regulates exon 10 splicing of mRNA precursor of Microtubule-associated protein tau (hereinafter sometimes to be abbreviated as "tau" or "MAPT") and use thereof.

BACKGROUND ART

In recent years, advances in medical and scientific technology have significantly extended life expectancy, especially in developed countries. Along therewith, however, various functional declines, diseases, and pathological conditions caused by aging of the brain, which have not been a problem in the past, have become major social problems. Among them, dementia greatly reduces the quality of life of the patient and also puts a heavy burden on the family members who care for the patient.

The symptoms of dementia are diverse, and include memory disorder, vision disorder, lalopathy, problem behavior, sleep disorder, depression symptom and the like. As degenerative diseases of the brain that cause such dementia, Alzheimer's disease, frontotemporal dementia (FTD), Lewy body dementia, cerebrovascular dementia, progressive supranuclear palsy (PSP), corticobasal degeneration (CBD) and the like are known, and most of them are sporadic cases with an unclear family history.

Dementia due to FTD is the second most common progressive dementia after Alzheimer's disease, particularly in Europe and the United States. The main feature of FTD is that the frontal lobe and lateral lobe are degenerative sites, and the histopathological findings thereof are three: frontal lobe degenerative type, Pick's disease type, and motor neuron disease type. Symptoms thereof include behavioral abnormalities caused by higher brain dysfunction, such as personality disorders and abnormal social behavior. However, the pathology of FTD is extremely complicated, and a fundamental treatment method has not yet been established because research on diagnostic methods and treatment methods has not been sufficiently conducted to date.

FTD has characteristics pathologically similar to Alzheimer's disease, PSP, and CBD. That is, accumulation of phosphorylated tau called neurofibrillary tangle is observed in the cytoplasm, neurite and the like of nerve cells at the diseased site, and these diseases are collectively called tauopathy. Tau is a protein that binds to microtubules, and six isoforms were found to exist by alternative splicing. It is roughly divided into 3-repeat tau (3R-tau) and 4-repeat tau (4R-tau) according to the number of repeats of the microtubule binding region on the C-terminal side. The ratio of these isoforms is known to vary pathologically depending on the disease, and it has been clarified that 4R-tau is dominant in FTD, PSP, and CBD, whereas mostly 1:1 in Alzheimer's disease.

On the other hand, FTD is known to have a disease spectrum similar to that of amyotrophic lateral sclerosis (ALS). The present inventors have been conducting research on FUS, which is a genetic and pathological factor common to these diseases, from the aspect of loss of function. As a result, they have found that FUS and its nuclear binding factor, SFPQ, both increase the 4R-tau/3R-tau isoform ratio, and this is the core of the pathology. They have clarified that normalizing this ratio dramatically improves the pathology. This pathology was widely confirmed in FTD, PSP, CBD autopsy brains (non-patent document 1). Therefore, an approach that normalizes the ratio of both isoforms while preserving the total tau expression level is important in treating tauopathy.

ASO, which is an artificial nucleic acid, forms Watson-Crick base pairs with RNA in the nucleus, and enables specific regulation of RNA expression that cannot be achieved with conventional low-molecular-weight compounds. RNA binding, nuclease resistance, pharmacokinetics, and pharmacological effects are enhanced by chemical modification. ASO is efficiently taken up by neurons and has a long half-life in the central neuron. Also, it shows less induction of immune response, shows highly-improved biological tolerability, permits administration to individual organs at various times and stages, and shows long-term pharmacological action in human. As one of the action mechanisms of ASO, ASO is known to regulate splicing of target genes and control expression levels of RNA splice isoforms through inhibition of the binding of trans factor to mRNA precursor, and the like by masking splicing cis sequence or inhibiting the formation of a higher-order structure.

Ionis Pharmaceuticals (US) has developed 2'-O-methoxyethyl (MOE)-modified ASO having the ability to regulate alternative splicing of tau (hereinafter to be also referred to as "tau splicing regulating ability") (patent document 1, non-patent document 2). In addition, there are reports relating to disease model cells and animal production methods via regulation of splicing by using MOE-modified ASO (patent document 2, non-patent documents 3, 4). However, conventional tau-targeting MOE-modified ASOs are insufficient in the effects in terms of tau splicing regulating potency and in vivo stability, and considered to require high dose administration to achieve therapeutic effects, which in turn may cause adverse events derived from ASO chemistry. In addition, there have been no reports on preclinical tests of pathological treatment using ASO for tauopathy such as FTD and the like.

Therefore, the development of a stronger and highly stable ASO for tau mRNA precursor has been desired.

DOCUMENT LIST

Patent Documents patent document 1: WO 2016/019063
patent document 2: US-A-2014/0298496

Non-Patent Documents non-patent document 1: Ishigaki, S. et al., Cell Rep. 2017 Jan. 31; 18 (5): 1118-1131.
non-patent document 2: Schoch, K. M. et al., Neuron. 2016 Jun. 1; 90 (5): 941-7.
non-patent document 3: Sahashi, K. et al., Genes Dev. 2012 Aug. 15; 26 (16): 1874-84.

non-patent document 4: Sahashi, K. et al., EMBO Mol Med. 2013 October; 5 (10): 1586-601.

SUMMARY OF INVENTION

Technical Problem

Therefore, the present invention aims to provide an ASO for tau mRNA precursor that is superior to conventionally-known MOE-modified ASO in tau splicing regulating potency and/or in vivo stability, and to provide a novel means of treating and/or preventing tauopathy including FTD by controlling 4R-tau/3R-tau isoform ratio by using the ASO.

Another purpose of the present invention is to provide novel cell and animal models of tauopathy by using the above-mentioned ASO for tau mRNA precursor, and to provide a means of exploring a therapeutic drug for tauopathy by using the model.

Solution to Problem

The present inventors have conducted intensive studies in an attempt to achieve the above-mentioned purposes, designed ASO complementary to a specific region within exon 10 of tau mRNA precursor (see FIG. 1), in which some of the constituent nucleotides are 2'-O, 4'-C-ethylene-bridged nucleic acids, ENA (registered trade mark), and introduced the ASO into cultured cells, and found that these ENA-modified ASOs have remarkably superior tau exon 10 skipping effects than respective MOE-modified ASOs having the same nucleotide sequences (see FIG. 2). The ENA-modified ASOs were given to mice by intraventricular bolus administration, and it was confirmed that a tau exon 10 skipping effect in the central neuron was sustained for at least 12 weeks and the ASOs showed good biological tolerability (see FIG. 8). Furthermore, it was found that the ENA-modified ASOs also show superior tau exon 10 skipping effects in the central neuron of sporadic FTD model mice obtained by knocking down FUS in human-tau mice in which the tau gene was replaced with human MAPT, regulate tau expression, and suppress dementia-like abnormal emotional behavior of the mouse (see FIGS. 11, 13).

On the other hand, they designed an ASO complementary to a specific region within the intron 10 near the exon 10 of the tau mRNA precursor, in which some of the constituent nucleotides thereof were similarly ENA-modified, and introduced the ASO into cultured cells. As a result, a 4R-tau/3R-tau isoform ratio increased, and it was clarified that these ENA-modified ASOs have a tau exon 10 inclusion effect (see FIG. 3).

Based on these findings, the present inventors concluded that an ENA-modified ASO for a specific region within exons 10 of tau mRNA precursor or a specific region within intron 10 adjacent thereto as a target sequence concurrently has high tau splicing regulating potency and in vivo stability, and thus can be a therapeutic and/or prophylactic drug for tauopathy associated with abnormal accumulation of 4R-tau or 3R-tau, and can be used for preparing novel cell and/or animal models of the tauopathy, as well as screening of candidates for a therapeutic and/or prophylactic drug for tauopathy by using the model, and completed the present invention.

That is, the present invention provides the following.

[1] A tau exon 10 skipping-promoting antisense oligonucleotide comprising at least one 2'-O, 4'-C-ethylene-bridged nucleic acid, and a nucleotide sequence complementary to a sequence consisting of at least 10 continuous nucleotides in a region consisting of the nucleotide sequence shown in SEQ ID NO: 44 in exon 10 of a tau mRNA precursor.

[2] The antisense oligonucleotide of [1], having a nucleotide length of 10-30 nucleotides.

[3] The antisense oligonucleotide of [1] or [2], comprising a nucleotide sequence complementary to a sequence consisting of at least 15 continuous nucleotides in the region of the 4th-38th nucleotides in the nucleotide sequence shown in SEQ ID NO: 44.

[4] The antisense oligonucleotide of [1] or [2], comprising the nucleotide sequence shown in any of SEQ ID NO: 2-21, 27-31 and 34-37 (wherein thymine may be uracil).

[5] The antisense oligonucleotide of [3], comprising the nucleotide sequence shown in any of SEQ ID NO: 3-20, 29, 30, 36 and 37 (wherein thymine may be uracil).

[6] The antisense oligonucleotide of any of [1] to [5], comprising 2'-O, 4'-C-ethylene-bridged nucleic acid as a pyrimidinenucleotide.

[7] The antisense oligonucleotide of any of [1] to [6], wherein at least one phosphodiester bond is phosphorothioated.

[8] A tau exon 10 skipping-promoting agent comprising the antisense oligonucleotide of any of [1] to [7].

[9] An agent for treating or preventing tauopathy associated with accumulation of 4R-tau, comprising the antisense oligonucleotide of any of [1] to [7].

[10] The agent of [9], wherein the tauopathy is frontotemporal dementia, frontotemporal lobar degeneration, corticobasal degeneration, progressive supranuclear palsy, Alzheimer's disease, senile dementia of the neurofibrillary tangle type, chronic traumatic encephalopathy or argyrophilic grain dementia.

[11] A method for producing a cell or animal model of tauopathy associated with accumulation of 3R tau, comprising incorporating the antisense oligonucleotide of any of [1] to [7] into a mammalian cell or a mammal.

[12] A cell or animal model of tauopathy associated with accumulation of 3R-tau, produced using the antisense oligonucleotide of any of [1] to [7].

[13] A method for screening for a therapeutic or prophylactic drug for tauopathy associated with accumulation of 3R-tau, comprising (1) a step of exposing the model of [12] to a test substance, (2) a step of testing one or more phenotypes of the tauopathy in the model, (3) a step of comparing the phenotypes with the model not exposed to the test substance, and (4) a step of selecting a test substance that improved the phenotype as a candidate for a therapeutic or prophylactic drug for the tauopathy.

[14] A tau exon 10 skipping-suppressing antisense oligonucleotide comprising at least one 2'-O, 4'-C-ethylene-bridged nucleic acid, and a nucleotide sequence complementary to a sequence consisting of at least 10 continuous nucleotides in a region consisting of the nucleotide sequence shown in SEQ ID NO: 45 in intron 10 of a tau mRNA precursor.

[15] The antisense oligonucleotide of [14], having a nucleotide length of 10-30 nucleotides.

[16] The antisense oligonucleotide of [14] or [15], comprising a nucleotide sequence complementary to a sequence consisting of at least 15 continuous nucleotides in the region of the 7th-27th nucleotides in the nucleotide sequence shown in SEQ ID NO: 45.

[17] The antisense oligonucleotide of [14] or [15], comprising the nucleotide sequence shown in any of SEQ ID NO: 22-24, 32, 33, 38 and 39 (wherein thymine may be uracil).

[18] The antisense oligonucleotide of [16], comprising the nucleotide sequence shown in SEQ ID NO: 22 or 23 (wherein thymine may be uracil).

[19] The antisense oligonucleotide of any of [14] to [18], comprising 2'-O, 4'-C-ethylene-bridged nucleic acid as a pyrimidinenucleotide.

[20] The antisense oligonucleotide of any of [14] to [19], wherein at least one phosphodiester bond is phosphorothioated.

[21] A tau exon 10 skipping-suppressing agent comprising the antisense oligonucleotide of any of [14] to [20].

[22] An agent for treating or preventing tauopathy associated with accumulation of 3R-tau, comprising the antisense oligonucleotide of any of [14] to [20].

[23] The agent of [22], wherein the tauopathy is Pick's disease.

[24] A method for producing a cell or animal model of tauopathy associated with accumulation of 4R tau, comprising incorporating the antisense oligonucleotide of any of [14] to [20] into a mammalian cell or a mammal.

[25] A cell or animal model of tauopathy associated with accumulation of 4R-tau, produced using the antisense oligonucleotide of any of [14] to [20].

[26] A method for screening for a therapeutic or prophylactic drug for tauopathy associated with accumulation of 4R-tau, comprising (1) a step of exposing the model of [25] to a test substance, (2) a step of testing one or more phenotypes of the tauopathy in the model, (3) a step of comparing the phenotypes with the model not exposed to the test substance, and (4) a step of selecting a test substance that improved the phenotype as a candidate for a therapeutic or prophylactic drug for the tauopathy.

Advantageous Effects of Invention

According to the ENA-modified ASO of the present invention, alternative splicing of tau exon 10 can be strongly and stably regulated, dose, administration frequency, and even manufacturing costs can be reduced, the 4R-tau/3R-tau isoform ratio can be normalized or accumulation of highly toxic 4-tau can be suppressed while suppressing the manifestation of invasive and adverse events, and tauopathy including sporadic FTD can be treated and prevented. In addition, cell and animal models of tauopathy can be produced using the ENA-modified ASO of the present invention, and the invention is useful for elucidation of the pathology of these diseases and screening for a therapeutic drug therefor.

BRIEF DESCRIPTION OF DRAWINGS

FIG. 7-1 shows the dose-dependent central neuron mouse tau exon 10 skipping effect by intraventricular bolus administration of two kinds of ENA-modified ASOs (NK-02, 05) to wild-type adult mice. NS indicates saline administration, and NK-41 indicates control ASO.

FIG. 7-2 shows the dose-dependent central neuron tau exon 10 skipping effect by intraventricular bolus administration of an ENA-modified ASO (NK-18) to adult tau model mice. NS indicates saline administration, and NK-41 indicates control ASO.

FIG. 11-1 shows the central neuron mouse tau exon 10 skipping effect by intraventricular bolus administration of an ENA-modified ASO to adult sporadic FTD model mice (humanized tau and FUS KD mouse). The left figure shows a decrease in 4R/3R-tau mRNA ratio by NK-05 (shFUS+NK-05, n=3), and the right figure shows a decrease in 4R/3R-tau protein ratio or a tendency thereof by NK-05, 18 (n=2) (shFUS+NK-05, 18, n=2). NS indicates saline administration, shCont indicates control AAV-shRNA-introduced mice, and NK-41 indicates control ASO.

FIG. 11-2 shows the central neuron mouse tau exon 10 skipping effect by intraventricular bolus administration of an ENA-modified ASO (NK-18) to adult sporadic FTD model mice (FUS KD mouse). The upper figure shows a decrease in 4R/3R-tau mRNA ratio by NK-18 (shFUS+NK-18, n=3), and the lower figure shows a decrease in 4R/3R-tau protein ratio by NK-18 (n=3) (shFUS+NK-18, n=3). shCont indicates control AAV-shRNA-introduced mice, and NK-41 indicates control ASO.

FIG. 12-1 confirms the tissue distribution in the central neuron by intraventricular bolus administration of FITC-labeled ENA-modified ASO (base sequence is the same as in NK-18) to adult mice. Wide distribution of ENA-modified ASO throughout the brain is shown. DAPI indicates nuclear staining and shows the shape of the entire brain here.

FIG. 12-2 shows the results of detection of the distribution of ASO in the brain and nerve cells by intraventricular bolus administration (NK-18, 50 μg administration) to mouse using an anti-ENA-modified ASO antibody.

FIG. 13-1 shows improvement in abnormal emotional behavior by intraventricular bolus administration of ENA-modified ASO to adult sporadic FTD model mice (humanized tau and FUS KD mouse). The abnormal emotional behavior was analyzed by an elevated plus maze test. shFUS increases staying time in the open arm (shFUS+NK-41, n=3), but NK-18 administration shortens staying time (shFUS+NK-18, n=4). NK-41 indicates control ASO.

FIG. 13-2 shows a treatment effect by intraventricular bolus administration of ENA-modified ASO to adult sporadic FTD model mice (FUS KD mouse). The elevated plus maze test showed improved entry-staying time in the Open/closed arm. NK-41 indicates control ASO. shCont+NK-41: n=28, shFUS+NK-41: n=27, shFUS+NK-18: n=26

DESCRIPTION OF EMBODIMENTS

1. Antisense Oligonucleotide Having Tau Splicing Regulating Ability

The present invention provides an antisense oligonucleotide (ASO) (hereinafter to be also referred to as "the ASO of the present invention") for tau mRNA precursor, which has a tau splicing regulating ability. The ASO of the present invention include one having an action of promoting tau exon 10 skipping, and one conversely having an action of suppressing tau exon 10 skipping. ASO having each action is explained below.

1-1. Tau Exon 10 Skipping-Promoting ASO

The present invention provides an antisense oligonucleotide for tau mRNA precursor, that promotes exon 10 skipping in alternative splicing of tau (hereinafter to be also referred to as "the promoting ASO of the present invention"). As used herein, "promotes exon 10 skipping" means that 4R-tau/3R-tau isoform ratio is reduced in a subject by introduction of ASO compared to that without ASO.

Figure 1:
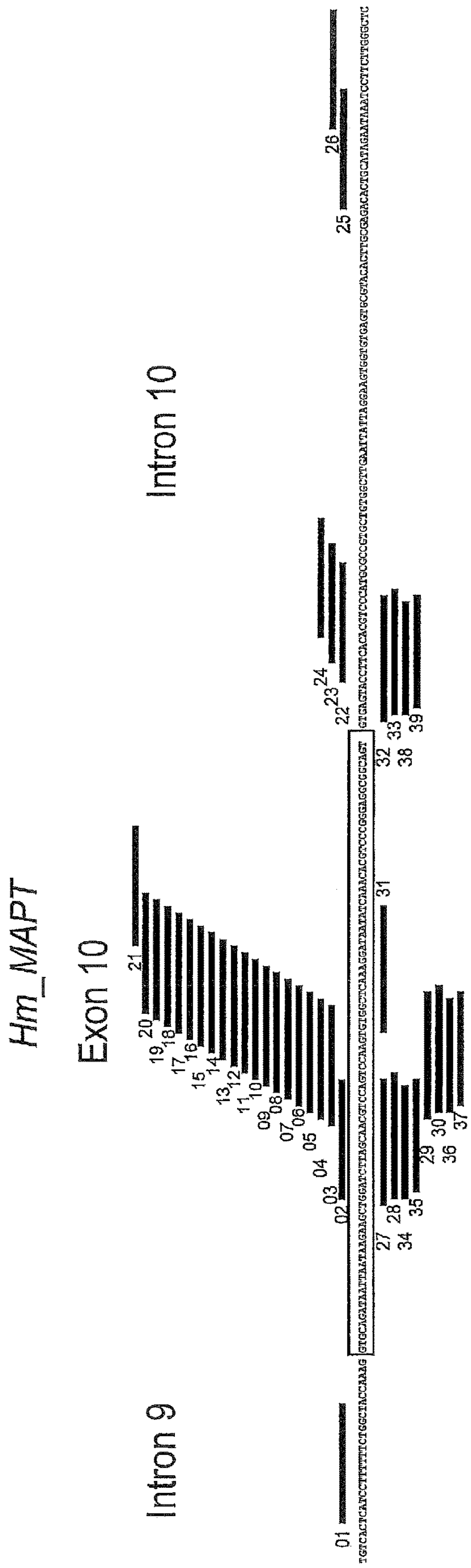
FIG. 1 shows the target regions of 39 kinds of ENA-modified ASOs (NK-01 to 39) on the tau gene (SEQ ID NO: 46). The part of the tau gene enclosed in a square is exon 10.

The region of the tau mRNA precursor targeted by the promoting ASO of the present invention is a region within exon 10 and consists of the nucleotide sequence shown in SEQ ID NO: 44 (gcaacgtccagtccaagtgtggctcaaaggataatatcaa). FIG. 1 shows the nucleotide sequence of exon 10 of human tau gene and vicinity thereof (part of intron 9 and part of intron 10) (SEQ ID NO: 46; corresponding to the sequence at positions 46010279-46010512 of the genomic sequence of human chromosome 17 (NC 000017.11) registered in the NCBI database). The region of the sequence enclosed in a square is exon 10 (region of nucleotide numbers 32-124 in the nucleotide sequence shown in SEQ ID NO: 46). The region targeted by the promoting ASO of the present invention is a region shown by nucleotide numbers 63-102 in the nucleotide sequence shown in SEQ ID NO: 46.

The promoting ASO of the present invention targets a sequence of at least 10 (e.g., 10, 15, 16, 17, 18, 19, 20 or more) continuous nucleotides in the above-mentioned target region.

In a preferred embodiment, the promoting ASO of the present invention targets a sequence consisting of at least 15 (e.g., 15, 16, 17, 18, 19, 20 or more) continuous nucleotides in the region of nucleotide numbers 4-38 (acgtccagtccaagtgtggctcaaaggataatatc; SEQ ID NO: 47) in the nucleotide sequence shown in SEQ ID NO: 44.

1-2. Tau Exon 10 Skipping-Suppressing Antisense Oligonucleotide (ASO)

The present invention also provides an antisense oligonucleotide for tau mRNA precursor, that suppresses exon 10 skipping in alternative splicing of tau (hereinafter to be also referred to as "the suppressing ASO of the present invention"). As used herein, "suppresses exon 10 skipping" means that 4R-tau/3R-tau isoform ratio is increased in a subject by introduction of ASO compared to that without ASO.

The region of the tau mRNA precursor targeted by the suppressing ASO of the present invention is a region within intron 10 near the exon 10 and consists of the nucleotide sequence shown in SEQ ID NO: 45 (tgagtaccttcacacgtcccatgcgccgtgc). In the nucleotide sequence (SEQ ID NO: 46) shown in FIG. 1, it is the region of nucleotide numbers 126-156.

The suppressing ASO of the present invention targets a sequence of at least 10 (e.g., 10, 15, 16, 17, 18, 19, 20 or more) continuous nucleotides in the above-mentioned target region.

In a preferred embodiment, the suppressing ASO of the present invention targets a sequence consisting of at least 15 (e.g., 15, 16, 17, 18, 19, 20) continuous nucleotides in the region of nucleotide numbers 7-27 (ccttcacacgtcccatgcgcc; SEQ ID NO: 48) in the nucleotide sequence shown in SEQ ID NO: 44.

1-3. Structural Characteristics of ASO of the Present Invention

The structural characteristics common to the promoting ASO of the present invention and the suppressing ASO of the present invention are explained below. The promoting ASO of the present invention and the suppressing ASO of the present invention are comprehensively referred to as "the ASO of the present invention".

The ASO of the present invention contains a nucleotide sequence complementary to a nucleotide sequence (target sequence) consisting of at least 10 (e.g., 10, 15, 16, 17, 18, 19, 20 or more), preferably not less than 15, continuous nucleotides in the above-mentioned each target region.

In the present invention, the "complementary nucleotide sequence" means not only a nucleotide sequence that is completely complementary to a target sequence (that is, hybridizes without a mismatch) but also even a nucleotide sequence including 1 to several (e.g., 2, 3, 4 or 5) mismatches as long as it can hybridize with a target sequence under physiological conditions of mammalian cells. For example, a sequence having identity of 80% or more (e.g., 85% or more, 90% or more, 95% or more, 96% or more, 97% or more, 98% or more, 99% or more), most preferably 100% identity, with a sequence completely complementary to the target sequence in tau mRNA precursor can be mentioned. The complementarity of individual bases is not limited to formation of Watson-Crick base pairs with the target base, and also includes formation of Hoogsteen base pairs and Wobble base pairs with the target base.

The length of the ASO of the present invention is not particularly limited and it is typically 10 to 50 nucleotides long, preferably 10 to 30 nucleotides long, more preferably 15 to 30 nucleotides long, and further preferably 18 to 22 nucleotides long.

Examples of the constituent unit of ASO of the present invention include ribonucleotide and deoxyribonucleotide. These nucleotides may be modified (modified nucleotide residues may be referred to as “modified nucleotide residues”) or unmodified (unmodified nucleotide residue is sometimes to be referred to as “unmodified nucleotide residue”).

The aforementioned nucleotide residue contains sugar, base, and phosphate as constituent elements. Ribonucleotide has a ribose residue as sugar and adenine (A), guanine (G), cytosine (C) or uracil (U) (which can also be replaced by thymine (T)) as a base. Deoxyribonucleotide residue has a deoxyribose residue as sugar and adenine (dA), guanine (dG), cytosine (dC) or thymine (dT) (which can also be replaced by uracil (dU)) as a base. In the following, nucleotides having adenine, guanine, cytosine, uracil, and thymine may be referred to as adenine nucleotide, guanine nucleotide, cytosine nucleotide, uracil nucleotide, and thymine nucleotide, respectively.

In the aforementioned non-modified nucleotide residue, the aforementioned each component is the same or substantially the same as, for example, that existing in nature, and preferably the same or substantially the same as that naturally occurring in the human body.

In the aforementioned modified nucleotide residue, for example, any of the constituent elements of the aforementioned non-modified nucleotide residue may be modified. In the present invention, “modification” includes, for example, substitution, addition and/or deletion of the aforementioned constituent elements, and substitution, addition and/or deletion of atoms and/or functional groups in the aforementioned constituent elements. Examples of the aforementioned modified nucleotide residue include naturally occurring nucleotide residue, artificially modified nucleotide residue, and the like. For the aforementioned naturally occurring modified nucleotide residue, Limbach et al (Limbach et al., 1994, Summary: the modified nucleosides of RNA, Nucleic Acids Res. 22:2183-2196) can be referred to. Examples of the aforementioned modified nucleotide residue include residues of the substitutes for the aforementioned nucleotide.

Examples of the modification of the aforementioned nucleotide residue include modification of a sugar-phosphate backbone (the backbone also includes a base) (hereinafter sugar-phosphate backbone).

In the aforementioned sugar-phosphate backbone, when the sugar is ribose, for example, the ribose residue can be modified. In the aforementioned ribose residue, for example, the 2'-position carbon can be modified. Specifically, for example, a hydroxyl group bound to the 2'-position carbon can be modified with a methyl group, or the hydroxyl group can be substituted with hydrogen or halogen such as fluoro. By substituting the hydroxyl group bound to the aforementioned 2'-position carbon with hydrogen, it is possible to substitute the ribose residue with deoxyribose. The aforementioned ribose residue can be substituted with its stereoisomer, for example, and may be substituted with, for example, an arabinose residue. In the following, a nucleic acid in which a hydroxyl group bonded to the 2'-position carbon of sugar is modified with a methoxy group as described above may be sometimes referred to as a 2'-O-methyl-modified nucleic acid. In the present invention, the “nucleic acid” includes nucleic acid monomers such as nucleotide and the like.

The aforementioned sugar-phosphate backbone may be substituted with, for example, a non-ribose residue (including non-deoxyribose residues) and/or a non-ribose phosphate backbone having a non-phosphate, and such substitution is also included in the modification of the sugar-phosphate backbone. The aforementioned non-ribose phosphate backbone may be, for example, the aforementioned sugar-phosphate backbone modified to be uncharged. Examples of an alternative of the aforementioned nucleotide having substitution with the aforementioned non-ribose phosphate backbone in include morpholino, cyclobutyl, and pyrrolidine. Other examples of the aforementioned alternative include artificial nucleic acid. Specific examples thereof include PNA (Peptide Nucleic Acid), Bridged Nucleic Acid (BNA) and the like. Examples of the BNA include Locked Nucleic Acid (LNA), 2'-O, 4'-C-ethylene-bridged nucleic acid (ENA) and the like. The specific structure (nucleoside moiety) of BNA including LNA and ENA that can be used in the present invention is shown below (cited from wo 2016/006697).

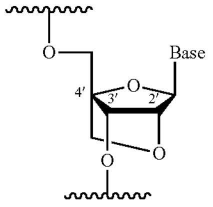

2′,4′-BNA(LNA)

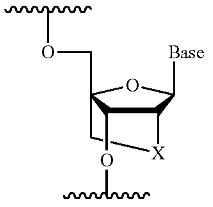

X = NR, S, $CH_2$, $CH_2CH_3$

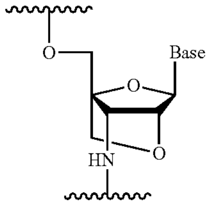

2′-amino-2′,4′-BNA

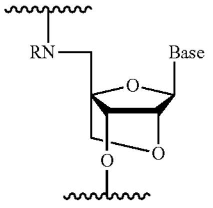

5′-amino-2′,4′-BNA

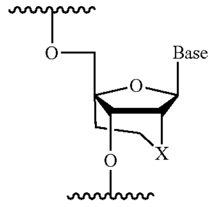

X = O, NH, $CH_2$, $CH_2CH_3$

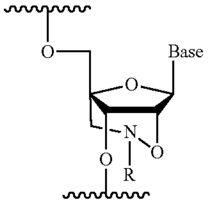

2′,4′-BNA$^{NC}$

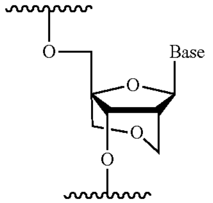

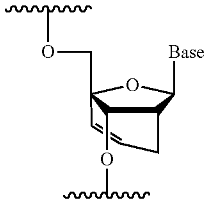

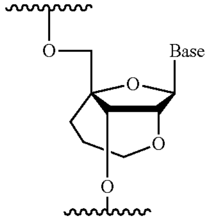

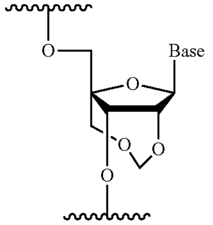

2′,4′-BNA$^{COC}$

-continued

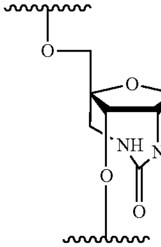

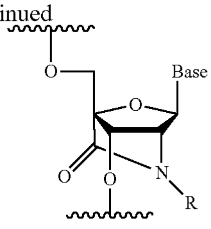

urea type 2′,4′-BNA wherein, R is a hydrogen atom, a branched or cyclic alkyl group having 1 to 7 carbon atoms, a branched or cyclic alkenyl group having 2 to 7 carbon atoms, an aryl group having 3 to 12 carbon atoms and optionally containing a hetero atom, an aralkyl group having an aryl moiety having 3 to 12 carbon atoms and optionally containing a hetero atom, or an amino-protecting group for nucleic acid synthesis. Preferably, R is a hydrogen atom, a methyl group, an ethyl group, an n-propyl group, an isopropyl group, a phenyl group, or a benzyl group, more preferably, R is a hydrogen atom or a methyl group, and Base is a base.

Of these, preferred is an ENA having the following nucleoside structure because it does not have extra modification other than efficient stabilization of type A (RNA type) structure.

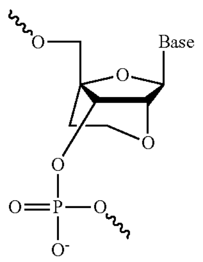

ENA wherein Base shows a base.

These artificial nucleic acids can be synthesized by referring to, for example, JP-A-2002-241393, JP-A-2000-297097 and the like.

The ASO of the present invention is characterized by containing at least one 2'-O, 4'-C-ethylene-bridged nucleic acid (ENA) as modified nucleotide residue. ENA modification can increase the binding force to the target RNA and in vivo metabolic stability by the bridged structure thereof. Preferably, the ASO of the present invention contains two or more ENA residues (e.g., 2, 3, 4, 5, 6, 7, 8, 9 or 10 or more). In one preferable embodiment, all pyrimidine (cytosine, thymine or uracil) nucleotides contained in the ASO of the present invention are ENA.

In one embodiment, the purine (adenine or guanine) nucleotide contained in the ASO of the present invention may be 2'-O-methyl-modified nucleic acid. Therefore, in one preferred embodiment, the ASO of the present invention may be ASO in which pyrimidine nucleotide is ENA and purine nucleotide is 2'-O-methyl-modified nucleic acid. In such ASO, the ratio of ENA and 2'-O-methyl-modified nucleic acid varies depending on the nucleotide sequence of ASO and is generally 1:4-4:1, preferably 2:3-3:2.

In the aforementioned sugar-phosphate backbone, for example, a phosphate group can be modified. In the aforementioned sugar-phosphate backbone, a phosphate group at the closest adjacency to the sugar residue is called an "α-phosphate group". The aforementioned α-phosphate group is charged negatively, and the electric charges are distributed evenly over two oxygen atoms that are not linked to the sugar residue. Among the four oxygen atoms in the aforementioned α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the aforementioned nucleotide residues hereinafter are referred to as "linking oxygens". For example, the aforementioned α-phosphate group is preferably modified to be uncharged, or to render the charge distribution between the aforementioned non-linking oxygen asymmetric.

In the aforementioned phosphate group, for example, the aforementioned non-linking oxygen(s) may be substituted. The aforementioned oxygen(s) can be substituted with, for example, any atom selected from S (sulfur), Se (selenium), B (boron), C (carbon), H (hydrogen), N (nitrogen), and OR (R is an alkyl group or an aryl group) and substitution with S is preferable. Either one or both of the aforementioned non-linking oxygens may be substituted, and it is preferable that either one or both of the non-linking oxygens be substituted with S. More specifically, as the aforementioned modified phosphate group, for example, phosphorothioates, phosphorodithioates, phosphoroselenates, boranophosphates, boranophosphate esters, hydrogen phosphonates, phosphoroamidates, alkyl or aryl phosphonates, and phosphotriesters and the like can be mentioned, and phosphorothioates and phosphorodithioates are preferred.

The aforementioned phosphate group may be substituted with a phosphorus-free linker. The aforementioned linker may be siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may be a methylenecarbonylamino group and a methylenemethylimino group. Alternatively, the aforementioned phosphate group may also be substituted with another phosphate-free linker. Examples of such linker include those described in "Med. Chem. Commun., 2014, 5, 1454-1471" and the like.

In a preferred embodiment, ½ or more, more preferably ⅔ or more, of the phosphate group contained in the ASO of the present invention is modified by one or more of the above-mentioned phosphate groups, and particularly preferably all phosphate groups are modified. For example, in the case of 18 mer ASO, 9 or more, preferably 12 or more, more preferably all phosphate groups, are, for example, phosphorothioated, phosphorodithioated or the like. Substitution of unbound oxygen at the phosphoric diester bond with sulfur atom is important in the tissue distribution of ASO.

In the ASO of the present invention, for example, at least one of a nucleotide residue at the 3'-terminus and a nucleotide residue at the 5'-terminus may be modified. For example, the nucleotide residue at either one of the 3'-terminus and the 5'-terminus may be modified, or the nucleotide residues at both the 3'-terminus and the 5'-terminus may be modified. The aforementioned modification may be, for example, as described above, and it is preferable to modify a phosphate group(s) at the end(s). For example, the entire aforementioned phosphate group may be modified, or one or more atoms in the aforementioned phosphate group may be modified. In the former case, for example, the entire phosphate group may be substituted or deleted.

Modification of the aforementioned nucleotide residue(s) at the end(s) may be, for example, addition of any other molecule. Examples of the aforementioned other molecule include functional molecules such as labeling substances as described below and protecting groups. Examples of the aforementioned protecting groups include S (sulfur), Si (silicon), B (boron), and ester-containing groups. The functional molecules such as the aforementioned labeling substances can be used, for example, in the detection and the like of the ASO of the present invention.

The aforementioned other molecule may be, for example, added to the phosphate group of the aforementioned nucleotide residue or may be added to the aforementioned phosphate group or the aforementioned sugar residue via a spacer. For example, the terminus atom of the aforementioned spacer can be added to or substituted for either one of the aforementioned linking oxygens of the aforementioned phosphate group, or O, N, S, or C of the sugar residue. The binding site in the aforementioned sugar residue preferably is, for example, C at the 3'-position, C at the 5'-position, or any atom bound thereto. For example, the aforementioned spacer can also be added to or substituted for a terminus atom of the aforementioned nucleotide alternative such as PNA.

The aforementioned spacer is not particularly limited, and examples thereof include $—(CH_2)_n—$, $—(CH_2)_nN—$, $—(CH_2)_nO—$, $—(CH_2)_nS—$, $O(CH_2CH_2O)_nCH_2CH_2OH$, abasic sugars, amide, carboxy, amine, oxyamine, oxyimine, thioether, disulfide, thiourea, sulfonamide, and morpholino, and also biotin reagents and fluorescein reagents. In the aforementioned formulae, n is a positive integer, and n=3 or 6 is preferable.

Other examples of the aforementioned molecule to be added to the end include dyes, intercalating agents (e.g., acridines), crosslinking agents (e.g., psoralen, mitomycin C), porphyrins (TPPC4, texaphyrin, sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrenebutyric acid, dihydrotestosterone, 1,3-Bis-O (hexadecyl)glycerol, a geranyloxyhexyl group, hexadecylglycerol, borneol, menthol, 1,3-propanediol, a heptadecyl group, palmitic acid, myristic acid, O3-(oleoyl) lithocholic acid, O3-(oleoyl) cholic acid, dimethoxytrityl, or phenoxazine), peptide complexes (e.g., Antennapedia peptide, Tat peptide), alkylating agents, phosphate, amino, mercapto, PEG (e.g., PEG-40K), MPEG, [MPEG] 2, polyamino, alkyl, substituted alkyl, radiolabeled markers, enzymes, haptens (e.g., biotin), transport/absorption promoting agent (e.g., aspirin, vitamin E, folic acid), and synthetic ribonucleases (e.g., imidazole, bisimidazole, histamine, imidazole clusters, acridine-imidazole complexes, $Eu^{3+}$ complexes of tetraazamacrocycles).

In the ASO of the present invention, the aforementioned 5'-terminus may be, for example, modified by a phosphate group or a phosphate group analog. Examples of the aforementioned phosphate group include 5'-monophosphate ($(HO)_2(O)P—O-5'$); 5'-diphosphate ($(HO)_2(O)P—O—P(HO)(O)—O-5'$); 5'-triphosphate ($(HO)_2(O)P—O—(HO)(O)P—O—P(HO)(O)—O-5'$); 5'-guanosine cap (7-methylated or non-methylated, 7m-G-O-5'-(HO)(O)P—O—(HO)(O)P—O—P(HO)(O)—O-5'); 5'-adenosine cap (Appp); any modified or unmodified nucleotide cap structure (N—O-5'-(HO)(O)P—O—(HO)(O)P—O—P(HO)(O)—O-5'); 5'-monothiophosphate (phosphorothioate: $(HO)_2(S)P—O-5'$); 5'-monodithiophosphate (phosphorodithioate: (HO)(HS) (S)P—O-5'); 5'-phosphorothiolate ($(HO)_2(O)P—S-5'$); sulfur substituted monophosphates, diphosphates and triphosphates (e.g., 5'-α-thiotriphosphate, 5'-γ-thiotriphosphate, and the like); 5'-phosphoramidates ($(HO)_2(O)P—NH-5'$, (HO) (NH2)(O)P—O-5'); 5'-alkylphosphonates (e.g., RP(OH)(O)—O-5', $(OH)_2(O)P-5'-CH_2$, where R is alkyl (e.g., methyl, ethyl, isopropyl, propyl, or the like)); and 5'-alkyletherphosphonates (e.g., RP(OH)(O)—O-5', where R is alkylether (e.g., methoxymethyl, ethoxymethyl, or the like)).

In the aforementioned nucleotide residue, the aforementioned base is not particularly limited and may be, for example, a natural base or a non-natural base. The aforementioned base may be, for example, a naturally-derived base or a synthetic base. As the aforementioned base, for example, a common base, a modified analog thereof, a universal base, and the like can be used.

Examples of the aforementioned base include purine bases such as adenine and guanine and the like, and pyrimidine bases such as cytosine, uracil, thymine and the like. Examples of the aforementioned base include, besides these, inosine, thymine, xanthine, hypoxanthine, nubularine, isoguanisine, tubercidine and the like. Examples of the aforementioned base include alkyl derivatives such as 2-aminoadenine, 6-methylated purine and the like; alkyl derivatives such as 2-propylated purine and the like; 5-halouracil and 5-halocytosine; 5-propynyluracil and 5-propynylcytosine; 6-azouracil, 6-azocytosine and 6-azothymine; 5-uracil (pseudouracil), 4-thiouracil, 5-halouracil, 5-(2-aminopropyl) uracil, 5-aminoallyluracil; 8-halogenated, aminated, thiolated, thioalkylated, hydroxylated and other 8-substituted purines; 5-trifluoromethylated and other 5-substituted pyrimidines; 7-methylguanine; 5-substituted pyrimidine; 6-aza pyrimidine; N-2, N-6, and O-6-substituted purines (including 2-aminopropyladenine); 5-propynyluracil and 5-propynylcytosine; dihydrouracil; 3-deaza-5-aza cytosine; 2-aminopurine; 5-alkyluracil; 7-alkylguanine; 5-alkylcytosine; 7-deazaadenine; N6, N6-dimethyladenine; 2,6-diaminopurine; 5-amino-allyl-uracil; N3-methyluracil; substituted 1,2,4-triazole; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl) uracil; 3-methylcytosine; 5-methylcytosine; N4-acetylcytosine; 2-thiocytosine; N6-methyladenine; N6-isopentyladenine; 2-methylthio-N6-isopentenyladenine; N-methylguanine; O-alkylated base and the like. Purine and pyrimidine include, for example, those disclosed in U.S. Pat. No. 3,687,808, "Concise Encyclopedia Of Polymer Science And Engineering", pages 858-859, ed. Kroschwitz J. I., John Wiley & Sons, 1990, and Englisch et al., Angewandte Chemie, International Edition, 1991, vol. 30, p. 613. The universal base means a nucleotide base analog capable of forming base pairs with adenine, guanine, cytosine, uracil, thymine and the like. Examples of the aforementioned universal base include, but are not limited to, C-phenyl, C-naphthyl and other aromatic derivatives, inosine, azolecarbozamide, nitroazole derivative (3-nitropyrrole, 4-nitroindole, 5-nitroindole, and 6-nitroindole etc.) (Loakes, 2001, Nucleic Acids Res. 29:2437), the bases described in WO 2007/026485 and the like.

Other examples of the aforementioned modified nucleotide residue include those having no base, i.e., those having an abasic sugar-phosphate backbone. Furthermore, as the aforementioned modified nucleotide residue, for example, the residue described in, for example, WO 2004/080406 can be used.

The ASO of the present invention may be labeled with, for example, a labeling substance. The aforementioned labeling substance is not particularly limited and, for example, fluorescent substance, dye, isotope and the like can be mentioned. Examples of the aforementioned labeling substance include fluorophore such as pyrene, TAMRA, fluorescein, Cy3 dye, Cy5 dye and the like, and examples of the aforementioned dye include Alexa dye such as Alexa488 and the like, and the like. Examples of the aforementioned isotope include stable isotope and radioisotope, and preferred is stable isotope. Since the aforementioned stable isotope has a low risk of exposure and does not require an exclusive facility, it is superior in handling property and can reduce the cost. In addition, the aforementioned stable isotope is also superior in properties as a tracer because, for example, it does not change the physical properties of the labeled compound. The aforementioned stable isotope is not particularly limited and, for example, $^{2}H$, $^{13}C$, $^{15}N$, $^{17}O$, $^{18}O$, $^{33}S$, $^{34}S$ and $^{36}S$ can be mentioned.

Specific examples of the promoting ASO of the present invention when, for example, the target sequence has a length of 18 mer include ASO containing the following nucleotide sequence (underlined part is a region complementary to the target region within exon 10 shown in SEQ ID NO: 44) as a complementary strand sequence to the target sequence:

(SEQ ID NO: 21)
ggacgtgtttgatattat (SEQ ID NO: 49)
gacgtgtttgatattatc (SEQ ID NO: 50)
acgtgtttgatattatcc (SEQ ID NO: 51)
cgtgtttgatattatcct (SEQ ID NO: 52)
gtgtttgatattatcctt (SEQ ID NO: 53)
tgtttgatattatccttt (SEQ ID NO: 54)
gtttgatattatcctttg (SEQ ID NO: 55)
tttgatattatcctttga (SEQ ID NO: 56)
ttgatattatcctttgag (SEQ ID NO: 57)
tgatattatcctttgagc (SEQ ID NO: 20)
gatattatcctttgagcc (SEQ ID NO: 19)
atattatcctttgagcca (SEQ ID NO: 18)
tattatcctttgagccac (SEQ ID NO: 17)

-continued attatcctttgagccaca (SEQ ID NO: 16)
ttatcctttgagccacac (SEQ ID NO: 15)
tatcctttgagccacact (SEQ ID NO: 14)
atcctttgagccacactt (SEQ ID NO: 13)
tcctttgagccacacttg (SEQ ID NO: 12)
cctttgagccacacttgg (SEQ ID NO: 11)
ctttgagccacacttgga (SEQ ID NO: 10)
tttgagccacacttggac (SEQ ID NO: 9)
ttgagccacacttggact (SEQ ID NO: 8)
tgagccacacttggactg (SEQ ID NO: 7)
gagccacacttggactgg (SEQ ID NO: 6)
agccacacttggactgga (SEQ ID NO: 5)
gccacacttggactggac (SEQ ID NO: 4)
ccacacttggactggacg (SEQ ID NO: 3)
cacacttggactggacgt (SEQ ID NO: 58)
acacttggactggacgtt (SEQ ID NO: 59)
cacttggactggacgttg (SEQ ID NO: 60)
acttggactggacgttgc (SEQ ID NO: 61)
cttggactggacgttgct (SEQ ID NO: 62)
ttggactggacgttgcta (SEQ ID NO: 63)
tggactggacgttgctaa (SEQ ID NO: 64)
ggactggacgttgctaag (SEQ ID NO: 65)
gactggacgttgctaaga (SEQ ID NO: 66)
actggacgttgctaagat (SEQ ID NO: 67)
ctggacgttgctaagatc (SEQ ID NO: 2)
tggacgttgctaagatcc (in the above-mentioned nucleotide sequences, thymine may be uracil).

In a preferred embodiment, specific examples of the promoting ASO of the present invention include ASO containing the nucleotide sequence shown in any of SEQ ID NO: 3-20, more preferably SEQ ID NO: 5-18 as a complementary strand sequence to the target sequence.

When the target sequence has a length of 19 mer, for example, ASO containing the nucleotide sequence shown in any of SEQ ID NO: 27-31, preferably SEQ ID NO: 29 or 30, as a complementary strand sequence to the target sequence can be mentioned.

(SEQ ID NO: 27)
tggacgttgctaagatcca (SEQ ID NO: 28)
ctggacgttgctaagatcc (SEQ ID NO: 29)
gccacacttggactggacg (SEQ ID NO: 30)
agccacacttggactggac (SEQ ID NO: 31)
tattatcctttgagccaca (in the above-mentioned nucleotide sequences, thymine may be uracil).

When the target sequence has a length of 17 mer, for example, ASO containing the nucleotide sequence shown in any of SEQ ID NO: 34-37, preferably SEQ ID NO: 36 or 37, as a complementary strand sequence to the target sequence can be mentioned.

(SEQ ID NO: 34)
ggacgttgctaagatcc (SEQ ID NO: 35)
tggacgttgctaagatc (SEQ ID NO: 36)
ccacacttggactggac (SEQ ID NO: 37)
gccacacttggactgga (in the above-mentioned nucleotide sequences, thymine may be uracil).

Specific examples of the suppressing ASO of the present invention when, for example, the target sequence has a length of 18 mer include ASO containing the following nucleotide sequence as a complementary strand sequence to the target sequence:

(SEQ ID NO: 24)
gcacggcgcatgggacgt (SEQ ID NO: 68)
cacggcgcatgggacgtg (SEQ ID NO: 69)
acggcgcatgggacgtgt (SEQ ID NO: 70)
cggcgcatgggacgtgtg (SEQ ID NO: 23)
ggcgcatgggacgtgtga (SEQ ID NO: 71)
gcgcatgggacgtgtgaa (SEQ ID NO: 72)
cgcatgggacgtgtgaag -continued (SEQ ID NO: 22)
gcatgggacgtgtgaagg (SEQ ID NO: 73)
catgggacgtgtgaaggt (SEQ ID NO: 74)
atgggacgtgtgaaggta (SEQ ID NO: 75)
tgggacgtgtgaaggtac (SEQ ID NO: 76)
gggacgtgtgaaggtact (SEQ ID NO: 77)
ggacgtgtgaaggtactc (SEQ ID NO: 78)
gacgtgtgaaggtactca (in the above-mentioned nucleotide sequences, thymine may be uracil).

In a preferred embodiment, specific examples of the suppressing ASO of the present invention include ASO containing the nucleotide sequence shown in any of SEQ ID NO: 22, 23, 71 and 72 as a complementary strand sequence to the target sequence.

When the target sequence has a length of 19 mer, for example, ASO containing the nucleotide sequence shown in SEQ ID NO: 32 or 33 as a complementary strand sequence to the target sequence can be mentioned.

(SEQ ID NO: 32)
ggacgtgtgaaggtactca (SEQ ID NO: 33)
gggacgtgtgaaggtactc (in the above-mentioned nucleotide sequences, thymine may be uracil).

When the target sequence has a length of 17 mer, for example, ASO containing the nucleotide sequence shown in SEQ ID NO: 38 or 39 as a complementary strand sequence to the target sequence can be mentioned.

(SEQ ID NO: 38)
gacgtgtgaaggtactc (SEQ ID NO: 39)
ggacgtgtgaaggtact (in the above-mentioned nucleotide sequences, thymine may be uracil).

The ASO of the present invention can be produced by a chemical synthesis method known per se. Examples thereof include a phosphoramidite method, an H-phosphonate method and the like. The chemical synthesis methods can be carried out, for example, using a commercially available automated nucleic acid synthesizer. When amidite is used, for example, RNA Phosphoramidites (2'-O-TBDMSi, trade name, Samchully Pharm. Co., Ltd.), ACE amidite, TOM amidite, CEE amidite, CEM amidite, TEM amidite and the like can be used as the commercially available amidite.

2. Use of ASO of the Present Invention 2-1. Tau Splicing Regulating Agent

The promoting ASO of the present invention can promote exon 10 skipping and lower the 4R-tau/3R-tau isoform ratio. On the other hand, the suppressing ASO of the present invention can suppress exon 10 skipping and increase the 4R-tau/3R-tau isoform ratio. Therefore, the present invention also provides a tau exon 10 skipping-promoting agent containing the promoting ASO of the present invention, and a tau exon 10 skipping-suppressing agent containing the suppressing ASO of the present invention (comprehensively to be also referred to as "the tau splicing regulating agent containing the ASO of the present invention", "the tau splicing regulating agent of the present invention").

The tau splicing regulating agent of the present invention can be introduced into a subject expressing the tau gene, for example, by contacting the subject with the ASO of the present invention alone or with a pharmacologically acceptable carrier. When the subject is an individual animal, the contact step can be performed by administering the tau splicing regulating agent of the present invention to the animal. When the subject is a culture of cell, tissue or organ derived from an animal, the contact step can be performed by adding the tau splicing regulating agent of the present invention to the medium of the culture.

To promote introduction of the ASO of the present invention into the target cell, the tau splicing regulating agent of the present invention may further contain a reagent for nucleic acid introduction. As the reagent for nucleic acid introduction, cationic lipids such as atelocollagen; liposome; nanoparticle; Lipofectin, lipofectamine, DOGS (Transfectam), DOPE, DOTAP, DDAB, DHDEAB, HDEAB, polybrene, poly(ethyleneimine) (PEI) and the like, and the like can be used.

2-2. Medicament Containing ASO of the Present Invention

Since the ASO of the present invention can promote or suppress exon 10 skipping and can control 4R-tau/3R-tau isoform ratio, it can be used for the treatment and/or prophylaxis of tauopathy with abnormal balance of 4R/3R-tau expression. That is, a medicament containing the promoting ASO of the present invention as an active ingredient can be used for the treatment and/or prophylaxis of tauopathy with 4R-tau accumulation. Examples of the tauopathy with 4R-tau accumulation include frontotemporal dementia (FTD), frontotemporal lobar degeneration (FTLD), corticobasal degeneration (CBD), progressive supranuclear palsy (PSP), Alzheimer's disease (AD), senile dementia of the neurofibrillary tangle type (SD-NFT), chronic traumatic encephalopathy, argyrophilic grain dementia and the like. On the other hand, a medicament containing the suppressing ASO of the present invention as an active ingredient can be used for the treatment and/or prophylaxis of tauopathy with 3R-tau accumulation. Examples of the tauopathy with 3R-tau accumulation include Pick's disease and the like.

The ASO of the present invention may be used alone, or may be formulated as a pharmaceutical composition together with a pharmaceutically acceptable carrier.

Examples of the pharmaceutically acceptable carrier include, but are not limited to, excipients such as sucrose, starch and the like, binders such as cellulose, methylcellulose and the like, disintegrants such as starch, carboxymethylcellulose and the like, lubricants such as magnesium stearate, Aerosil and the like, flavoring agents such as citric acid, menthol and the like, preservatives such as sodium benzoate, sodium bisulfite and the like, stabilizers such as citric acid, sodium citrate and the like, suspending agents such as methylcellulose, polyvinyl pyrrolidone and the like, dispersing agents such as surfactant and the like, diluents such as water, saline and the like, base wax and the like.

To promote introduction of the ASO of the present invention into the target cell, the medicament of the present invention may further contain a reagent for nucleic acid introduction. As the reagent for nucleic acid introduction, those similar to the aforementioned can be used.

In addition, the medicament of the present invention may be a pharmaceutical composition in which the ASO of the present invention is encapsulated in a liposome. Liposome is a fine closed vesicle having an inner phase surrounded by one or more lipid bilayers, and can generally retain a water-soluble substance in the inner phase and a liposoluble substance in the lipid bilayer. In the present specification, when "encapsulated" is used, the ASO of the present invention may be held in the liposome inner phase or in the lipid bilayer. The liposome to be used in the present invention may be unilamellar or multilamellar, and the particle size can be appropriately selected from, for example, the range of 10-1000 nm, preferably 50-300 nm. In consideration of the deliverability to the target tissue, the particle size may be, for example, not more than 200 nm, preferably not more than 100 nm.

Examples of a method for encapsulating a water-soluble compound such as oligonucleotides in a liposome include a lipid film method (vortex method), a reversed-phase evaporation method, a surfactant-removing method, a freeze-thawing method, a remote loading method, and the like. However, the method is not limited to these and any known method can be appropriately selected.

The medicament of the present invention can be orally or parenterally administered to a mammal (e.g., human, rat, mouse, guinea pig, rabbit, sheep, horse, swine, bovine, monkey). Parenteral administration is desirable.

A preparation preferable for parenteral administration (e.g., subcutaneous injection, intramuscular injection, topical injecting (e.g., intraventricular administration), intraperitoneal administration and the like) is an aqueous or non-aqueous isotonic aseptic injection liquid which may contain antioxidant, buffer, bacteriostatic agent, isotonizing agent and the like. In addition, an aqueous or non-aqueous aseptic suspension agent can be mentioned which may contain suspending agent, solubilizer, thickener, stabilizer, preservative and the like. The preparation can be enclosed in a container in a unit dose or multiple doses like ampoules and vials. Alternatively, the active ingredient and a pharmaceutically acceptable carrier can also be lyophilized and stored in a state only requiring dissolving or suspending in a suitable sterile vehicle immediately before use.

The content of the ASO of the present invention in the pharmaceutical composition is, for example, about 0.1 to 100 wt % of the whole pharmaceutical composition.

While the administration route of the medicament of the present invention is not particularly limited as long as a therapeutically or prophylactically effective amount of the ASO of the present invention is delivered and introduced into the cells of the target tissue, that is, the central neuron tissue, in which 4R or 3R tau is accumulated, intraventricular administration is preferable.

While the dose of the medicament of the present invention varies depending on the administration objective, administration method, the kind of target disease, severity, condition of the subject of administration (sex, age, body weight and the like), for systemic administration to an adult, for example, 2 nmol/kg or more and 50 nmol/kg or less as a single dose of the ASO of the present invention is generally desirable; for topical administration, 1 pmol/kg or more and 10 nmol/kg or less as a single dose of the ASO of the present invention is generally desirable. Such amounts can be administered at the intervals of, for example, 1-6 months, preferably 2-4 months, more preferably about 3 months.

Since the ASO of the present invention is remarkably superior in tau splicing regulating potency and in vivo stability as compared with conventionally known ASOs, it can afford a therapeutic and/or prophylactic effect with a low dose and low administration frequency, which in turn can improve the QOL of patients, reduce medical expenses, and suppress the manifestation of adverse events.

The medicament of the present invention can be used in combination with other therapeutic agents for tauopathy, such as tau hyperphosphorylation inhibitors (e.g., GSK3β inhibitors (e.g., lithium, tideglusib), etc.), tau aggregation inhibitors (e.g., methylene blue, etc.), and the like. These concomitant drugs can be formulated together with the medicament of the present invention and administered as a single preparation, or can also be formulated separately from the medicament of the present invention and administered simultaneously or with a time difference in a route the same as or different from the route of the medicament of the present invention. The dose of these concomitant drugs may be an amount generally used when the drug is administered alone, or may be reduced from an amount generally used.

A therapeutic and/or prophylactic method including administering an effective amount of the ASO of the present invention or the medicament of the present invention to a mammal (animal to be the subject of treatment or prophylaxis) is also included in the present invention. Specific examples of the effective amount, dose, mammal and other matters are as described in 2-2.

2-3. Production of Disease Model and Utilization Thereof

Since the ASO of the present invention can promote or suppress exon 10 skipping and can control 4R-tau/3R-tau isoform ratio, cells or animal models of tauopathy associated with abnormal balance of 4R/3R-tau expression can be produced by incorporating the ASO into cultured cells or experimental animals. That is, a model of tauopathy associated with the accumulation of 3R-tau can be produced by incorporating the promoting ASO of the present invention. Examples of the tauopathy associated with accumulation of 3R-tau include Pick's disease and the like. On the other hand, a model of tauopathy associated with the accumulation of 4R-tau can be produced by incorporating the suppressing ASO of the present invention. Examples of the tauopathy associated with accumulation of 4R-tau include FTD, CBD, PSP, argyrophilic grain dementia and the like.

The cell or animal into which the ASO of the present invention is incorporated is not particularly limited, and examples include experimental animals such as mammals other than human, preferably mouse, rat, hamster, guinea pig, rabbit, monkey and the like, and cell, tissue and organ derived from these animals which may be primary culture or passage culture. Preferred are establish cultured cells, and more preferred are human cultured cells. In addition, it may be a cell obtained by inducing differentiation from a stem cell such as a pluripotent stem cell by a method known per se. Examples of such stem cell include embryonic stem cells (ES cell), induced pluripotent stem cell (iPS cell), pluripotency germ stem cell, embryonic germ cell (EG cell), neural stem cell, mesenchymal stem cell and the like.

The cell or animal into which the ASO of the present invention is incorporated may be a normal animal or a cell derived from the normal animal, or an animal having tauopathy with overexpression of tau or abnormal balance of 4R/3R-tau expression, or a cell derived therefrom, or the like. Examples of the animal having tauopathy with overexpression of tau or abnormal balance of 4R/3R-tau expression include, but are not limited to, Alzheimer's disease model mice with tau gene introduced thereinto, sporadic FTD model mice in which FUS is knocked down, and the like. Alternatively, cultured cells into which the tau gene has been introduced or cultured cells in which FUS has been knocked down may also be used.

Examples of the method for incorporating the ASO of the present invention into cells or the like include a method in which the ASO of the present invention is added to the medium for the cells or the like (transfection or the like). The ASO of the present invention can be incorporated into an individual animal by administering the ASO of the present invention to the animal. The administration method is not particularly limited as long as the ASO of the present invention in an amount effective for causing manifestation of the pathology can be delivered and introduced into the cells of the tissue in which 4R or 3R-tau is accumulated, i.e., the central neuron tissue, in the target disease. Preferred is intraventricular administration.

Whether the animal, cell or the like incorporating the ASO of the present invention is the disease model of interest can be confirmed by measuring the balance of 4R/3R-tau expression in the central nerve, the cell thereof or the like of the animal, or examining one or more phenotypes of the disease, such as behavioral abnormality, presence or absence of pathology manifestation, degree thereof and the like in the animal.

The cell or animal model of tauopathy obtained as described above can be used, for example, for screening for a therapeutic and/or prophylactic drug for tauopathy of. That is, the present invention provides a method for screening for a therapeutic or prophylactic drug for tauopathy associated with accumulation of 3R-tau or 4R-tau, including (1) a step of exposing the above-mentioned model to a test substance, (2) a step of testing one or more phenotypes of the tauopathy in the model, (3) a step of comparing the phenotypes with the model not exposed to the test substance, and (4) a step of selecting a test substance that improved the phenotype as a candidate for a therapeutic or prophylactic drug for the tauopathy.

In step (1), the model can be exposed to the test substance in the same manner as in the incorporation of the ASO of the present invention, according to the form of the model.

In step (2), the balance of expression of one or more phenotypes of tauopathy, such as balance of 4R/3R-tau expression, and the presence or absence of manifestation of abnormal behavior and the degree thereof in the animal, are tested as in the above-mentioned confirmation of the establishment of the model.

As the model not exposed to the test substance and used as a control in step (3), a different model prepared by the same method or the same model before exposure to the test substance may be used.

As the result of the comparison in step (3), a test substance that significantly improved the phenotype of tauopathy can be selected as a candidate substance for a therapeutic and/or prophylactic drug for the tauopathy.

While the present invention is explained in detail in the following by referring to Examples, the present invention is not limited thereto.

EXAMPLE

Example 1 Production of ASO for Tau mRNA Precursor

Combining bibliographic consideration and prediction tools, ASOs consisting of 39 kinds of sequences (NK-01-39) that form base pairs with the sequences inside tau exon 10 or vicinity thereof (intron 9 or intron 10) and ASO consisting of non-specific sequences (NK-40-43) as the control were designed. FIG. 1 shows the target regions of the ASOs of NK-01-39. The nucleotide sequence of each ASO is as follows.

```
NK-01:
                                    (SEQ ID NO: 1)
agccagaaaaaaggatga

NK-02:
                                    (SEQ ID NO: 2)
tggacgttgctaagatcc

NK-03:
                                    (SEQ ID NO: 3)
cacacttggactggacgt

NK-04:
                                    (SEQ ID NO: 4)
ccacacttggactggacg

NK-05:
                                    (SEQ ID NO: 5)
gccacacttggactggac

NK-06:
                                    (SEQ ID NO: 6)
agccacacttggactgga

NK-07:
                                    (SEQ ID NO: 7)
gagccacacttggactgg

NK-08:
                                    (SEQ ID NO: 8)
tgagccacacttggactg

NK-09:
                                    (SEQ ID NO: 9)
ttgagccacacttggact

NK-10:
                                   (SEQ ID NO: 10)
tttgagccacacttggac

NK-11:
                                   (SEQ ID NO: 11)
ctttgagccacacttgga

NK-12:
                                   (SEQ ID NO: 12)
cctttgagccacacttgg

NK-13:
                                   (SEQ ID NO: 13)
tcctttgagccacacttg

NK-14:
                                   (SEQ ID NO: 14)
atcctttgagccacactt

NK-15:
                                   (SEQ ID NO: 15)
tatcctttgagccacact

NK-16:
                                   (SEQ ID NO: 16)
ttatcctttgagccacac

NK-17:
                                   (SEQ ID NO: 17)
attatcctttgagccaca

NK-18:
                                   (SEQ ID NO: 18)
tattatcctttgagccac

NK-19:
                                   (SEQ ID NO: 19)
```

-continued

```
atattatcctttgagcca

NK-20:
                                   (SEQ ID NO: 20)
gatattatcctttgagcc

NK-21:
                                   (SEQ ID NO: 21)
ggacgtgtttgatattat

NK-22:
                                   (SEQ ID NO: 22)
gcatgggacgtgtgaagg

NK-23:
                                   (SEQ ID NO: 23)
ggcgcatgggacgtgtga

NK-24:
                                   (SEQ ID NO: 24)
gcacggcgcatgggacgt

NK-25:
                                   (SEQ ID NO: 25)
tttattctatgcagtgtc

NK-26:
                                   (SEQ ID NO: 26)
gcccaagaaggatttatt

NK-27:
                                   (SEQ ID NO: 27)
tggacgttgctaagatcca

NK-28:
                                   (SEQ ID NO: 28)
ctggacgttgctaagatcc

NK-29:
                                   (SEQ ID NO: 29)
gccacacttggactggacg

NK-30:
                                   (SEQ ID NO: 30)
agccacacttggactggac

NK-31:
                                   (SEQ ID NO: 31)
tattatcctttgagccaca

NK-32:
                                   (SEQ ID NO: 32)
ggacgtgtgaaggtactca

NK-33:
                                   (SEQ ID NO: 33)
gggacgtgtgaaggtactc

NK-34:
                                   (SEQ ID NO: 34)
ggacgttgctaagatcc

NK-35:
                                   (SEQ ID NO: 35)
tggacgttgctaagatc

NK-36:
                                   (SEQ ID NO: 36)
ccacacttggactggac

NK-37:
                                   (SEQ ID NO: 37)
gccacacttggactgga

NK-38:
                                   (SEQ ID NO: 38)
gacgtgtgaaggtactc

NK-39:
                                   (SEQ ID NO: 39)
ggacgtgtgaaggtact
```

-continued

```
NK-40:
                                   (SEQ ID NO: 40)
catctaagcaacaattga

NK-41:
                                   (SEQ ID NO: 41)
ctcttgacgcacatctgg

NK-42:
                                   (SEQ ID NO: 42)
ttccctgaaggttcctcc

NK-43:
                                   (SEQ ID NO: 43)
tcagtaaacttgacacca
```

According to a conventional method, ASOs having each of the above-mentioned nucleotide sequences were synthesized. ENA was used for cytosine and thymine, and all phosphate groups were phosphorothioated. As comparison examples, ASO with all nucleotide residues modified with MOE was also synthesized for NK-05, 12, 16, 18 and 41.

Example 2 Comparison of ENA-Modified ASO and MOE-Modified ASO in Tau Splicing Regulating Potency The tau splicing regulating potency was compared between 4 kinds of ENA-modified ASOs having the nucleotide sequences of SEQ ID NO: 5, 12, 16 and 18 and 4 kinds of MOE-modified ASOs having the same sequence.

Figure 2:
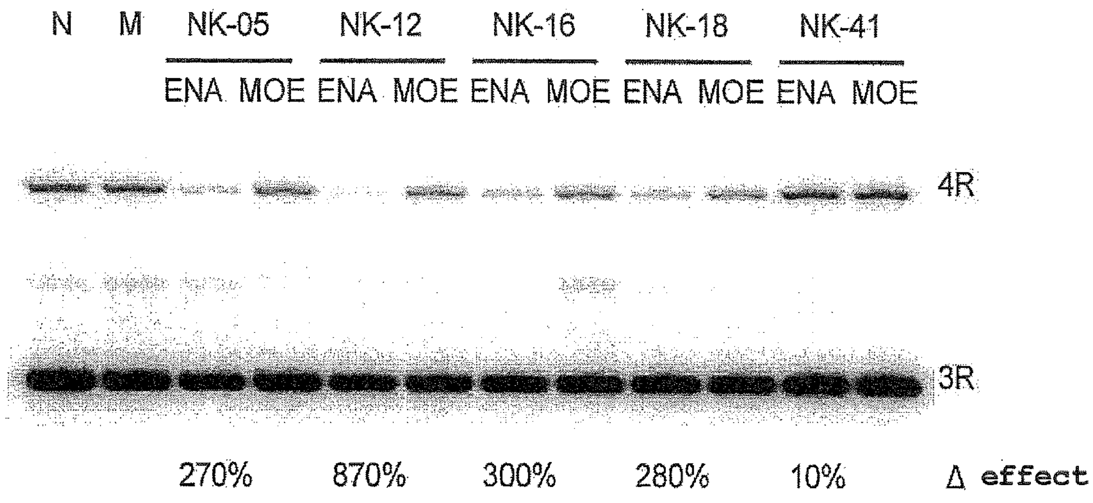
FIG. 2 shows the superiority of 4 kinds of ENA-modified ASOS (NK-05, 12, 16, 18) to MOE-modified ASO in HEK293 cell-endogenous tau exon 10 skipping efficacy. In the Figure, N indicates no transfection treatment, M indicates mock transfection, and NK-41 indicates control ASO.

Human cultured cells (HEK293 cells) were transfected with 50 nM of each ASO by using Lipofectamine 2000 (#11668027, Thermo). 48 hr after transfection, the cultured cells were lysed with TRIzol (#15596018, Thermo) and then RNA was extracted using RNeasy Mini Kit (#74104, Qiagen). The extracted mRNA was reverse transcribed into cDNA by using ImProm-II Reverse Transcriptase (#M314A, Promega) and, using this as a template, semi-quantitative RT-PCR using radioisotope was performed. RT-PCR was performed using CCATGCCAGACCTGAAGAAT (SEQ ID NO: 79) as the forward primer, TGCTCAGGTCAACTGGTTTG (SEQ ID NO: 80) as the reverse primer, AmpliTaq DNA Polymerase (#N8080152, Thermo), and P-32 Deoxycytidine 5'-triphosphate (#NEG013H, PerkinElmer). The results are shown in FIG. 2.

In all sequences, the tau exon 10 skipping effect of ENA-modified ASO was remarkably higher than that of MOE-modified ASO having the same sequence (about 3- to about 9-fold).

Figure 3:
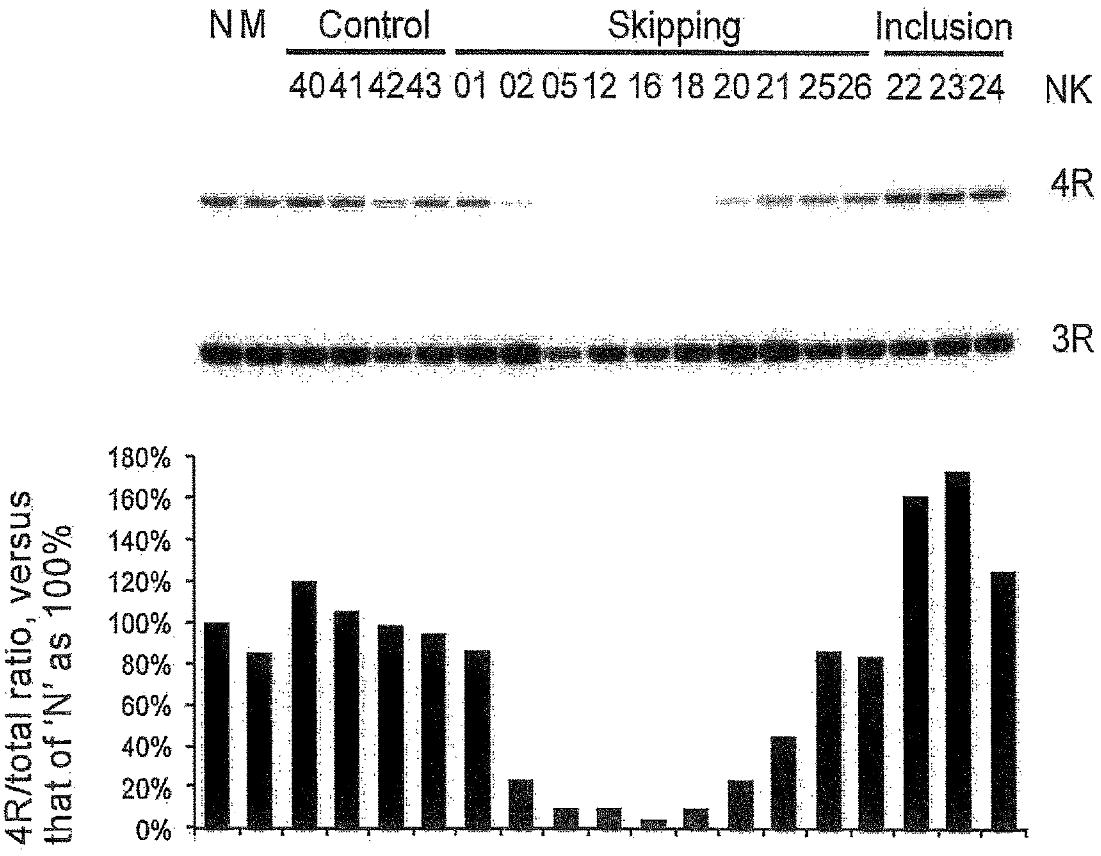
FIG. 3 shows the skipping or inclusion effect of 17 kinds of ENA-modified ASOs (NK-01, 02, 05, 12, 16, 18, 20-26, 40-43) on HEK293 cell-endogenous tau exon 10. N indicates no transfection treatment, and M indicates mock transfection.

Example 3 Identification of Promoting ASO and Suppressing ASO and Target Regions Thereof Thirteen kinds of the ASOs (NK-01, 02, 05, 12, 16, 18, 20-26) for tau mRNA precursor prepared in Example 1 and 4 kinds of the control ASOs (NK-40-43) were each introduced into human cultured cells (HEK293 cells) in the same manner as in Example 2, and the effect on endogenous tau exon 10 skipping was measured by RT-PCR to screen for ASO having tau splicing regulating ability. The results are shown in FIG. 3.

Six kinds of ASOs (NK-02, 05, 12, 16, 18, 20) having a target sequence in a specific region within exon 10 showed a high tau exon 10 skipping-promoting effect. On the other hand, 3 kinds of ASOs (NK-22, 23, 24) having a target sequence in a specific region within intron 10 showed a high tau exon 10 skipping-suppressing (exon 10 inclusion) effect.

Example 4 Detailed Study of Promoting ASO

Figure 4:
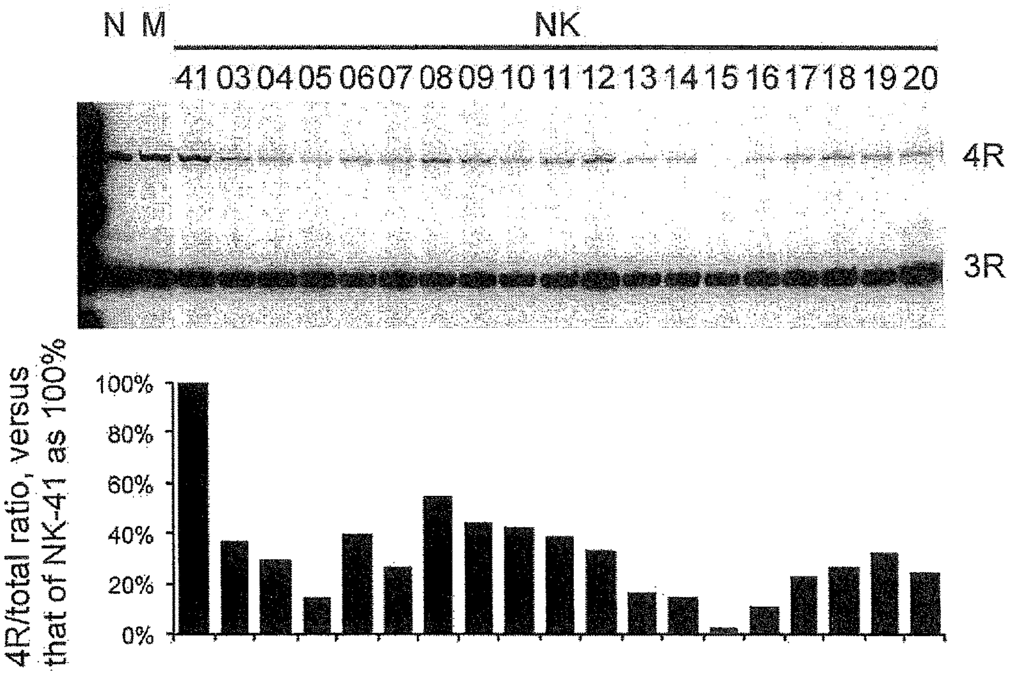
FIG. 4 shows the skipping effect of 18 kinds of ENA-modified ASOs (NK-03-20) on HEK293 cell-endogenous tau exon 10. N indicates no transfection treatment, M indicates mock transfection, and NK-41 indicates control ASO.

Eighteen kinds in total of 18 mer ASOs (NK-03-20) and complementary to the tau mRNA precursor target regions of the 6 kinds of highly efficient ASOs identified in Example 3 were each introduced into human cultured cells (HEK293 cells) in the same manner as in Example 2, and the effect on endogenous tau exon 10 skipping was measured by RT-PCR to screen for ASO having tau splicing regulating ability. The results are shown in FIG. 4.

Five kinds of ASOs (NK-05, 13-16) showed a particularly high tau exon 10 skipping-promoting effect.

Example 5 Study of Optimal Length of Promoting ASO

Figure 5:
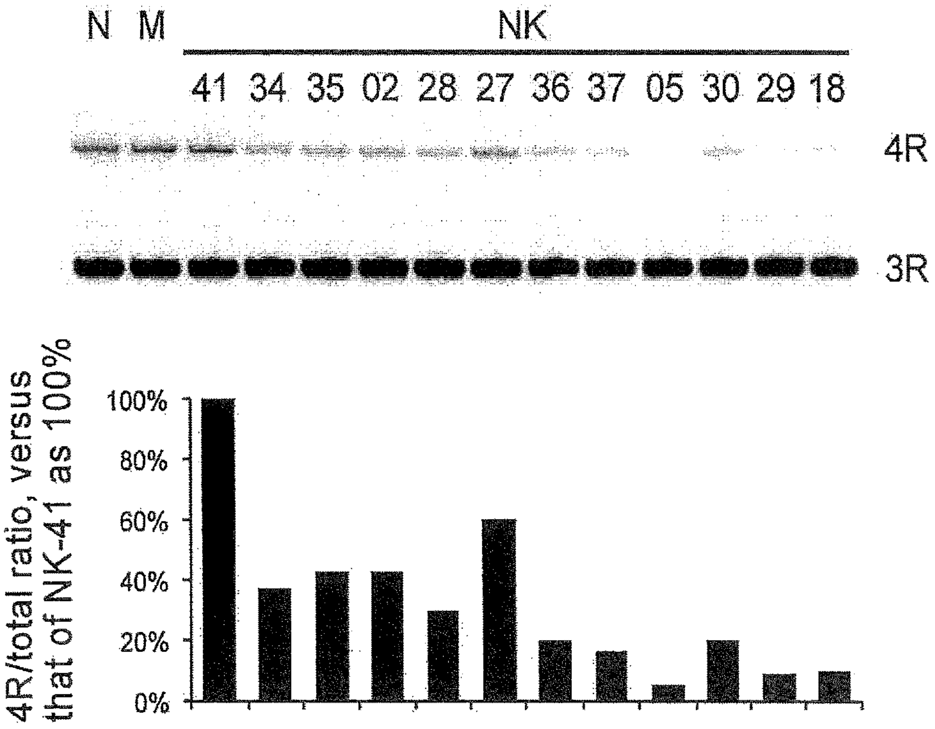
FIG. 5 shows the skipping effect of 11 kinds of ENA-modified ASOs (NK-02, 05, 18, 27-30, 34-37) on HEK293 cell-endogenous tau exon 10. N indicates no transfection treatment, M indicates mock transfection, and NK-41 indicates control ASO.

Eleven kinds in total of ASOs (NK-02, 05, 18, 27-30, 34-37) including 17 mer ASOs (NK-34-37) obtained by excluding one terminal nucleotide of one of the two kinds of highly efficient 18 mer ASOs (NK-02, 05) identified in Example 3, and 19 mer ASOs (NK-27-30) obtained by adding 1 nucleotide to one terminal of the same highly efficient 18 mer ASO were each introduced into human cultured cells (HEK293 cells) in the same manner as in Example 2, and the effect on endogenous tau exon 10 skipping was measured by RT-PCR to screen for ASO having tau splicing regulating ability. The results are shown in FIG. 5.

NK-05 ASO showed a high tau exon 10 skipping-promoting effect, and the optimality of 18 mer length was suggested.

Figure 6:
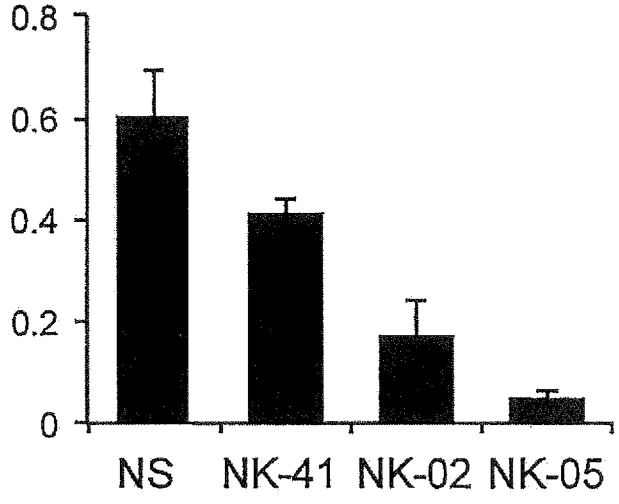
FIG. 6 shows the skipping effect of two kinds of ENA-modified ASOs (NK-02, 05) on central neuron mouse tau exon 10 by intraventricular bolus administration to wild-type neonatal mice. NS indicates saline administration, and NK-41 indicates control ASO.

Example 6-1 Effect of Promoting ASO on Wild-Type Mouse (1) Wild-type neonatal mice (line: C57BL/6J, sex: male or female (n=3 each)) were administered with 10 μg each of NK-02 and 05 ASOs by intraventricular bolus administration. One week after administration, RNA was extracted from the central neuron by the same method as in Example 2, 4R-tau and 3R-tau mRNAs were measured by RT-PCR, and the ratios thereof were calculated. The results are shown in FIG. 6.

NK-02, 05 ASOs remarkably promoted mouse tau exon 10 skipping in the central neuron of neonatal mice.

Figure 7:
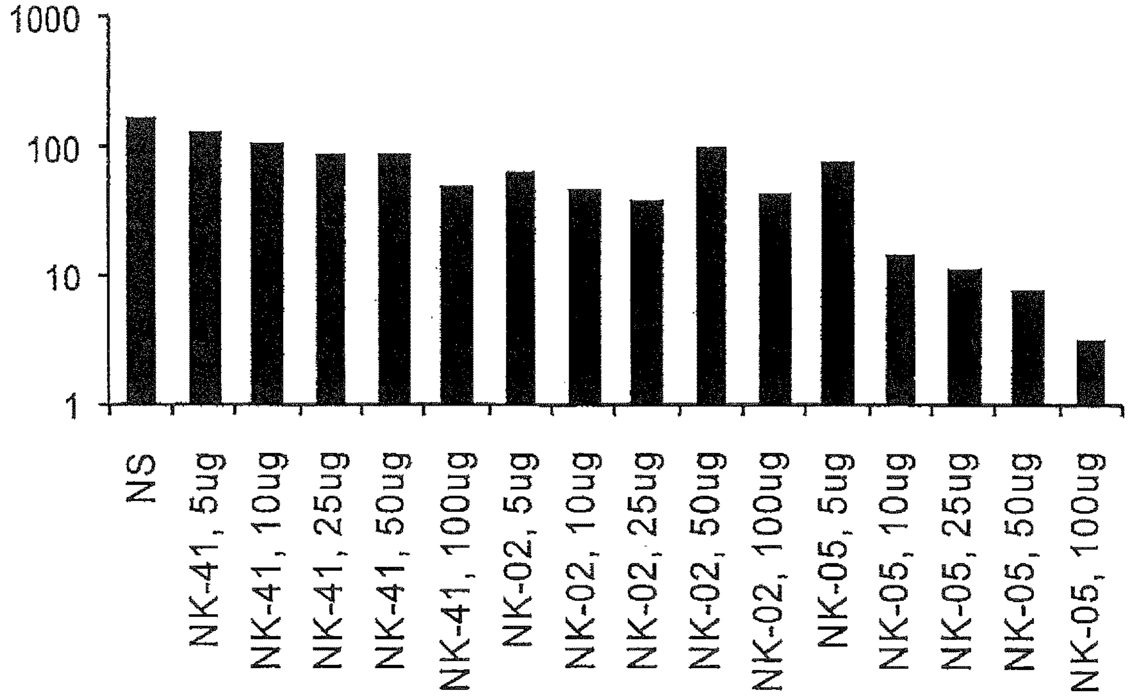
Figure 1:
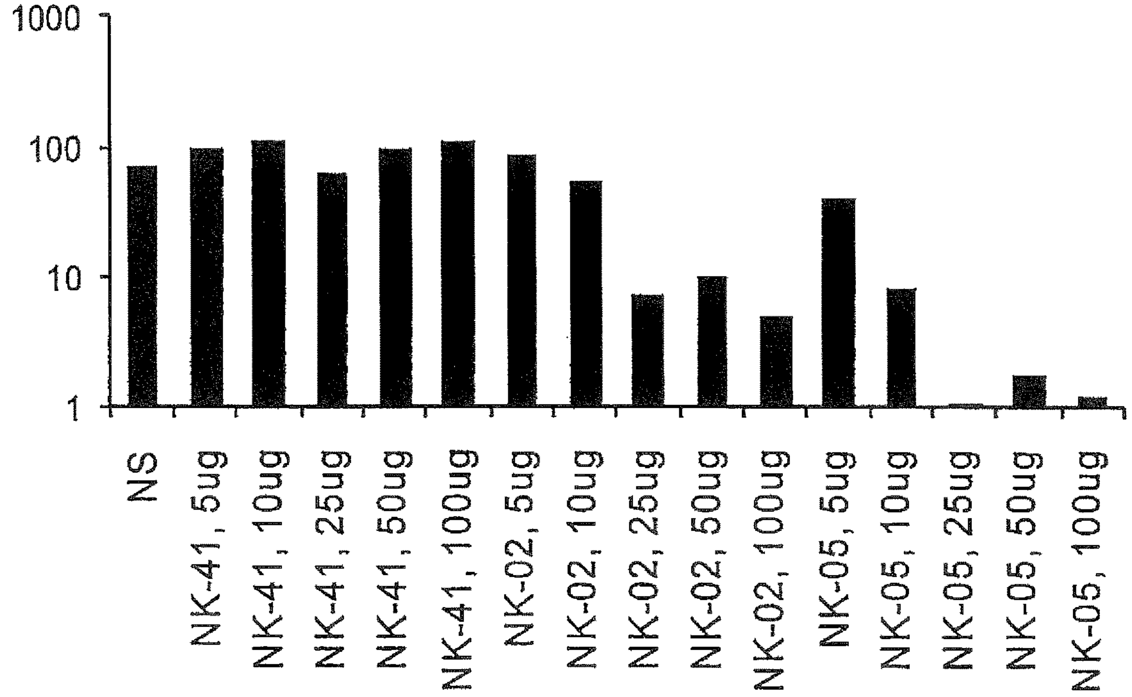
Figure 7:
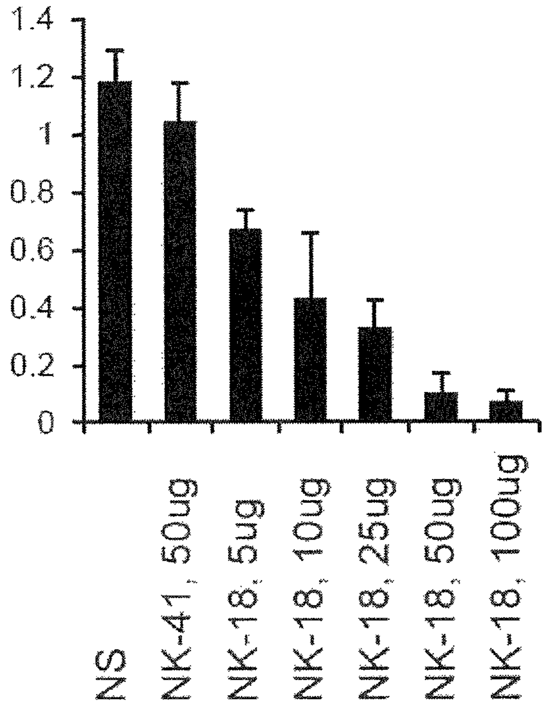
Figure 2:
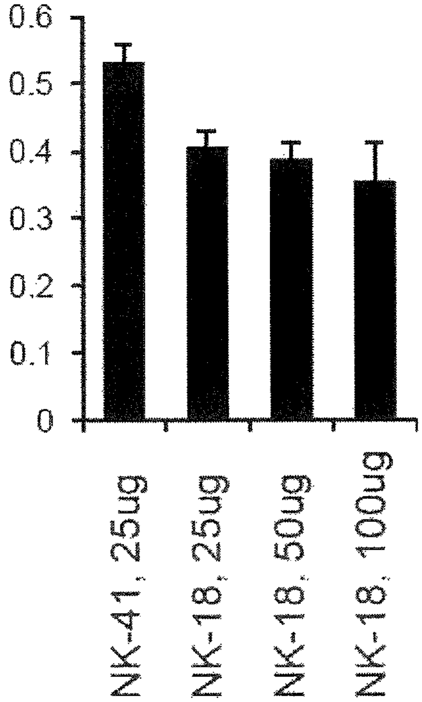

(2) Wild-type adult mice (line: C57BL/6J, sex: male, about 12-week-old (n=1 each)) were administered with various concentrations (5, 10, 25, 50, 100 μg) of NK-02, 05 ASOs by intraventricular bolus administration. One week after administration, RNA was extracted from the cerebral cortex and hippocampus by the same method as in Example 2, 4R-tau and 3R-tau mRNAs were measured by RT-PCR, and the ratios thereof were calculated. The results are shown in FIG. 7-1.

NK-05 ASO promoted mouse tau exon 10 skipping in a dose-dependent manner in both the cerebral cortex and hippocampus. NK-02 ASO also promoted mouse tau exon 10 skipping in a dose-dependent manner in hippocampus; however, the effect was higher with NK-05 ASO.

Figure 8:
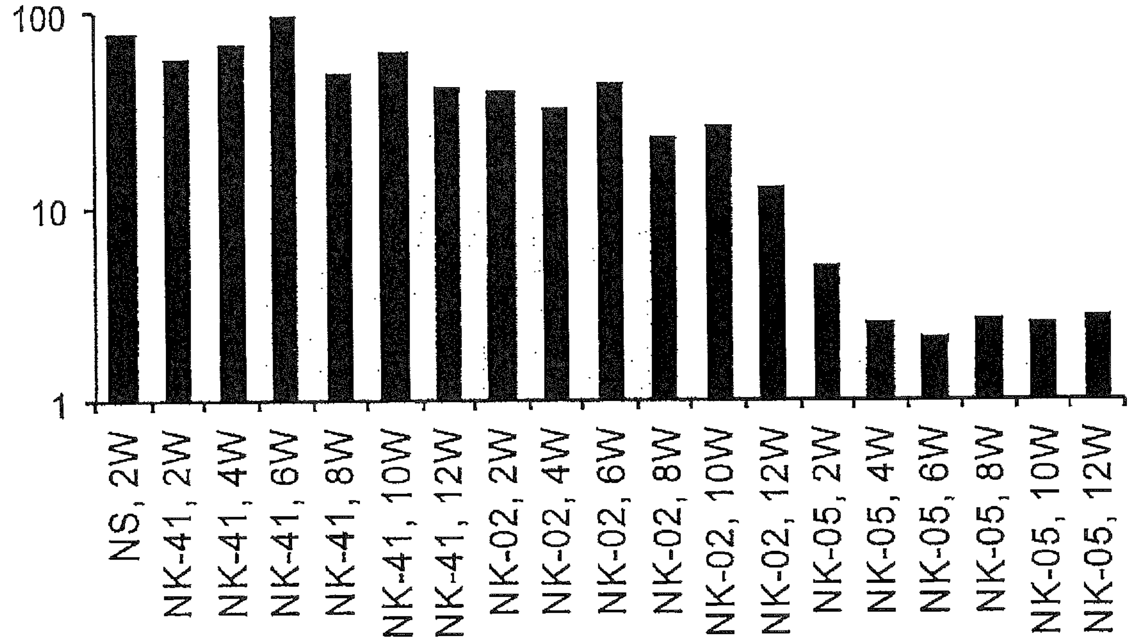
FIG. 8 shows the sustained central neuron mouse tau exon 10 skipping effect by intraventricular bolus administration of two kinds of ENA-modified ASOs (NK-02, 05) to wild-type adult mice. NS indicates saline administration, and NK-41 indicates control ASO.
Figure 8:
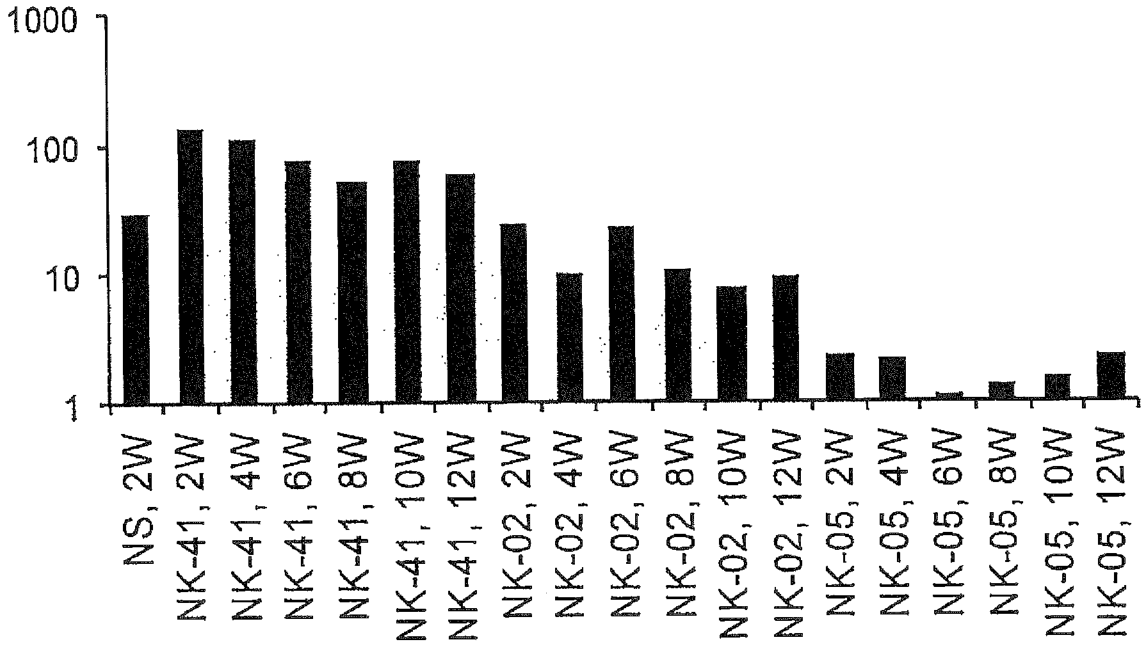

(3) Then, wild-type adult mice (line: C57BL/6J, sex: male, about 12-week-old (n=1 each)) were administered with 100 μg of NK-02, 05 ASOs by intraventricular bolus administration. 2, 4, 6, 8, 10, 12 weeks after administration, RNA was extracted from the cerebral cortex and hippocampus by the same method as in Example 2, 4R-tau and 3R-tau mRNAs were measured by RT-PCR, and the ratios thereof were calculated. The results are shown in FIG. 8.

The effect of NK-02, 05 ASOs were sustained for a long term of at least 12 weeks. During this period, good biological tolerability was also observed.

Example 6-2 Dose-Dependent Effect of Promoting ASO on Tauopathy Model Mouse (1) Humanized tau mice (hT-PAC-N) having human tau transgene (source: Jackson Laboratory, sex: male, 12-week-old (n=5 each)) were administered with various concentrations (5, 10, 25, 50, 100 μg) of NK-18 ASO by intraventricular bolus administration. Six weeks after administration, RNA was extracted from the cerebral cortex by the same method as in Example 2, 4R-tau and 3R-tau mRNAs were measured by RT-PCR, and the ratios thereof were calculated. The results are shown in FIG. 7-2 (upper Fig.)

NK-18 ASO promoted mouse tau exon 10 skipping in a dose-dependent manner in the cerebral cortex.

(2) Humanized tau mice (hT-PAC-N) having human tau transgene (source: same as in (1), sex: male, 12-week-old (n=3 each)) were administered with various concentrations (25, 50, 100 μg) of NK-18 ASO by intraventricular bolus administration. Six weeks after administration, protein was extracted from the hippocampus by using RIPA buffer. Using 20 μg each of the protein, anti-RD3 antibody (#05-803, Millipore), and anti-RD4 antibody (#05-804, Millipore), Western blot was performed, 4R-tau and 3R-tau proteins were measured, and the ratios thereof were calculated. The results are shown in FIG. 7-2 (lower Fig.).

NK-18 showed a decrease in the 4R/3R-tau protein ratio in the central neuron of the model mice.

Figure 9:
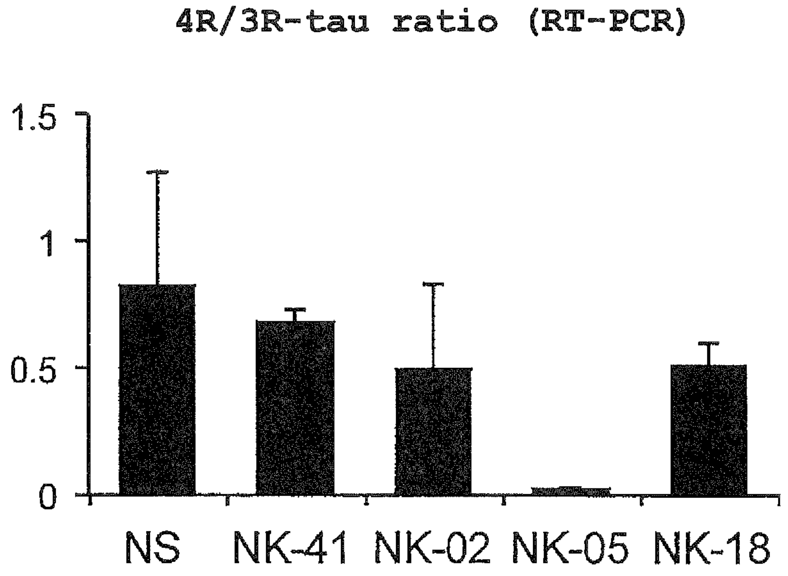
FIG. 9 shows the central neuron human tau transgene exon 10 skipping effect by intraventricular bolus administration of three kinds of ENA-modified ASOs (NK-02, 05, 18) to neonatal tau model mice. NS indicates saline administration, and NK-41 indicates control ASO.

Example 7 Effect of Promoting ASO on Tauopathy Model Mouse (1) Humanized tau mice (hT-PAC-N) having human tau transgene (source: Jackson Laboratory, neonate of (#17326), sex: male or female (n=4-6 each)) were administered with 10 μg of NK-02, 05, 18 ASOs by intraventricular bolus administration. One week after administration, RNA was extracted from the central neuron by the same method as in Example 2, 4R-tau and 3R-tau mRNAs were measured by RT-PCR, and the ratios thereof were calculated. The results are shown in FIG. 9 (neonate).

NK-05 ASO remarkably promoted mouse tau exon 10 skipping in the central neuron of neonatal model mice. NK-02, 18 ASOs also showed tendency to promote tau exon 10 skipping, though a significant difference was absent.

Figure 10:
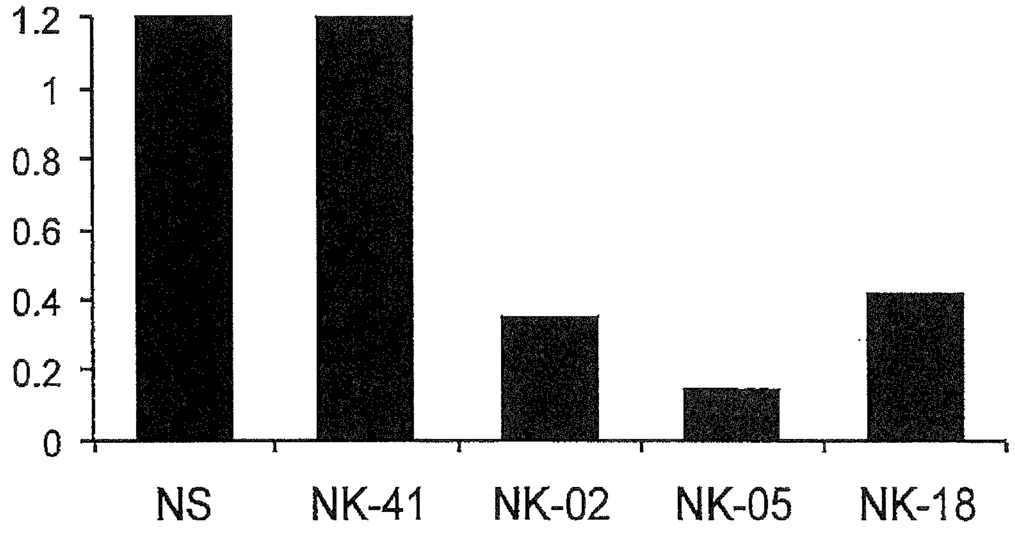
FIG. 10 shows the central neuron human tau transgene exon 10 skipping effect by intraventricular bolus administration of three kinds of ENA-modified ASOs (NK-02, 05, 18) to adult tau model mice. NS indicates saline administration, and NK-41 indicates control ASO.
Figure 10:
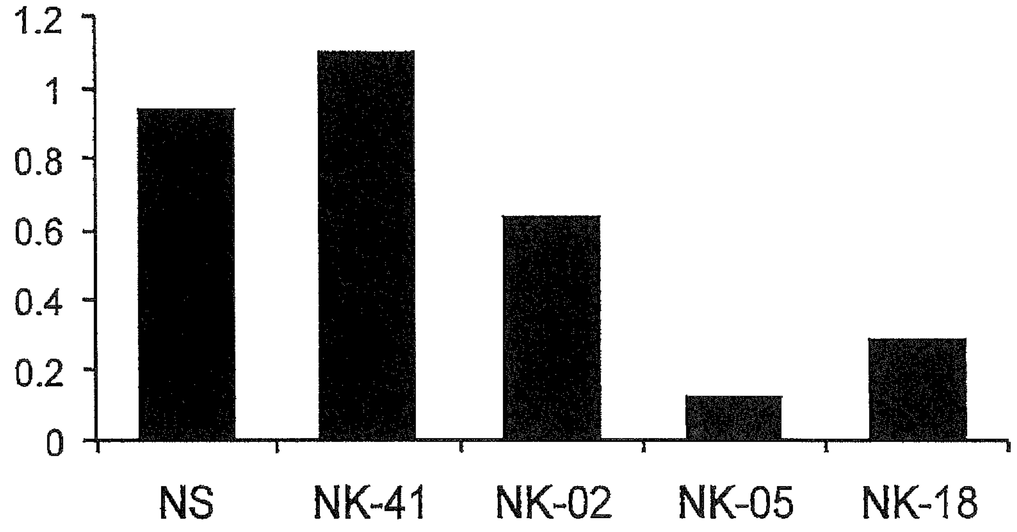

(2) Humanized tau mice (hT-PAC-N) having human tau transgene (source: same as in (1), sex: male, 12-week-old (n=1 each)) were administered with 100 μg of NK-02, 05, 18 ASOs by intraventricular bolus administration. Six weeks after administration, RNA was extracted from the cerebral cortex and hippocampus (adult) by the same method as in Example 2, 4R-tau and 3R-tau mRNAs were measured by RT-PCR, and the ratios thereof were calculated. The results are shown in FIG. 10 (adult).

In adult model mice, all of NK-02, NK-05 and NK-18 ASOs remarkably promoted mouse tau exon 10 skipping in both the cerebral cortex and hippocampus. Among others, NK-05 ASO most strongly promoted tau exon 10 skipping.

(3) Sporadic FTD model mice into which AAV-shRNA was introduced to knock down FUS (source: produced by injecting AAV-shFUS into hT-PAC-N of (1)) (Cell Reports (2017) 18:1118-1131), sex: male, 6-week-old) were administered with 100 μg of NK-05, 18 ASOs by intraventricular bolus administration. Six weeks after administration, RNA was extracted from the central neuron by the same method as in Example 2, 4R-tau and 3R-tau mRNAs were measured by RT-PCR, and the ratios thereof were calculated. The results are shown in FIG. 11-1.

Figures 1, 11:
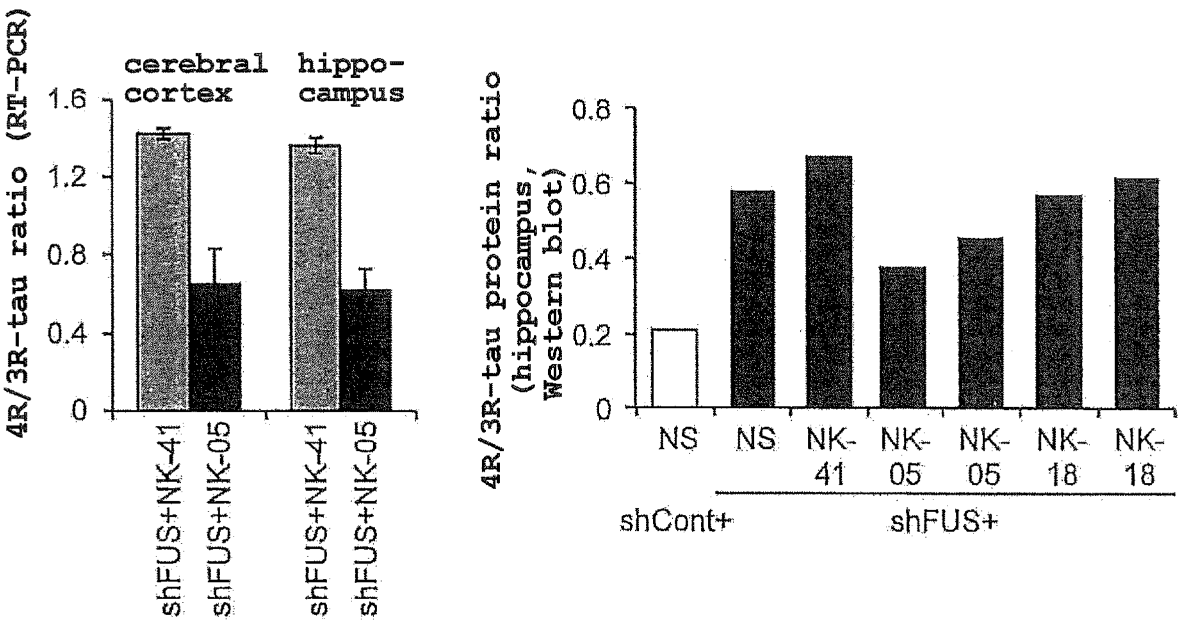
Figure 11:
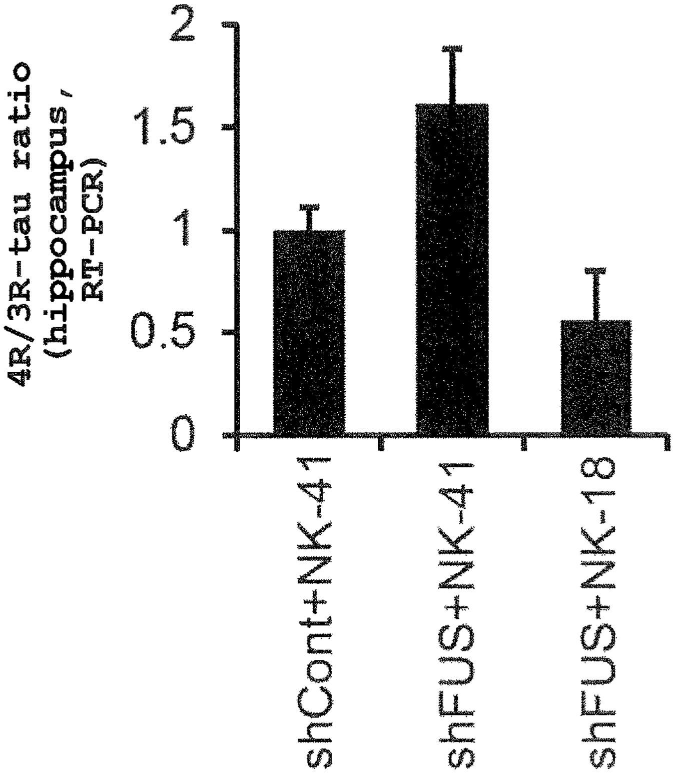
Figure 2:
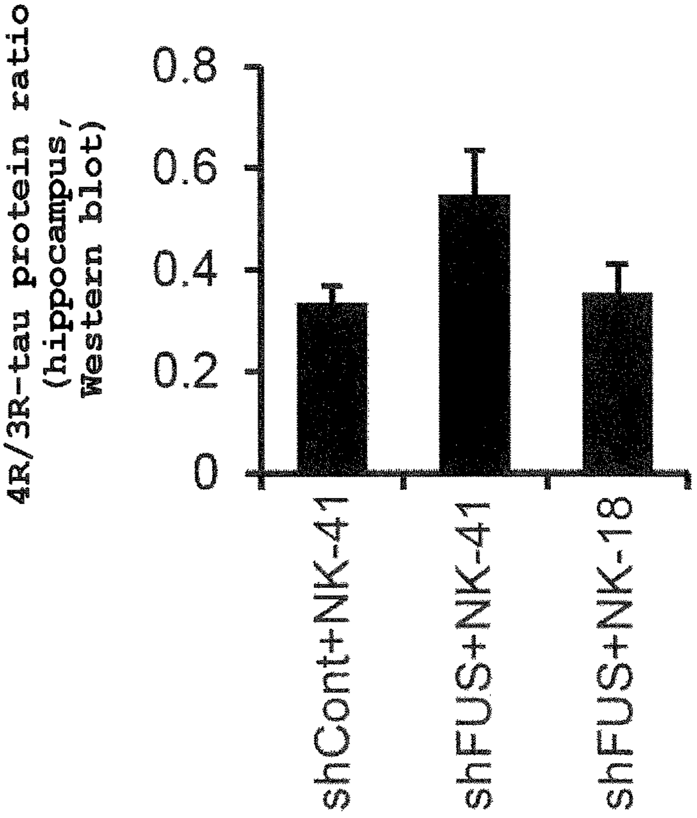

NK-05 (n=3) remarkably decreased the 4R/3R-tau mRNA ratio in the central neuron of the model mice (FIG. 11-1, left).

Similarly, protein was extracted from the hippocampus by using RIPA buffer. Using 20 μg each of the protein, anti-RD3 antibody (#05-803, Millipore), and anti-RD4 antibody (#05-804, Millipore), Western blot was performed, 4R-tau and 3R-tau proteins were measured, and the ratios thereof were calculated. NK-05, 18 (n=2) showed a decrease or a tendency thereof in the 4R/3R-tau protein ratio in the central neuron of the model mice (FIG. 11-1, right).

(4) Mice with control AAV-shRNA (shCont) introduced thereinto or sporadic FTD model mice into which AAV-shRNA was introduced to knock down FUS (source: same as in (3), sex: male, 6-week-old (n=3 each)) were administered with 50 μg of NK-18 ASO by intraventricular bolus administration. Six weeks after administration, RNA was extracted from the hippocampus by the same method as in Example 2, 4R-tau and 3R-tau mRNAs were measured by RT-PCR, and the ratios thereof were calculated. The results are shown in FIG. 11-2 (upper Fig.).

NK-18 remarkably decreased the 4R/3R-tau mRNA ratio in the central neuron of the model mice.

Similarly, protein was extracted from the hippocampus by using RIPA buffer. Using 20 μg each of the protein, anti-RD3 antibody (#05-803, Millipore), and anti-RD4 antibody (#05-804, Millipore), Western blot was performed, 4R-tau and 3R-tau proteins were measured, and the ratios thereof were calculated. The results are shown in FIG. 11-2 (lower Fig.).

NK-18 showed a decrease in the 4R/3R-tau protein ratio in the central neuron of the model mice.

Example 8 Intracerebral Distribution and Uptake into Nerve Cells of ASO (1) Fluorescent (FITC)-conjugated NK-18 ASO (100 μg) was administered to wild-type adult mice by intraventricular bolus administration. One week after administration, the distribution of the ASO in each part of the brain was examined. The results are shown in FIG. 12-1.

Extensive intracerebral distribution of ASO, and high uptake of ASO into nerve cells could be confirmed. DAPI indicates nuclear staining, and shows the shape of the entire brain here.

(2) NK-18 ASO (50 μg) was administered by intraventricular bolus administration. Using anti-ENA-modified ASO antibody (ordered antibody, Mabel), the distribution of the ASO in the brain and nerve cells was examined one month after administration. The results are shown in FIG. 12-2.

Extensive intracerebral distribution of ASO, and high uptake of ASO into nerve cells could be confirmed.

Example 9 ASO Treatment Effect on Sporadic FTD Model Mouse by ASO

This Example shows improvement of abnormal emotional behavior by intraventricular bolus administration of 100 μg of NK-18 to adult sporadic FTD model mice (humanized tau and FUS KD mice).

Figures 1, 13:
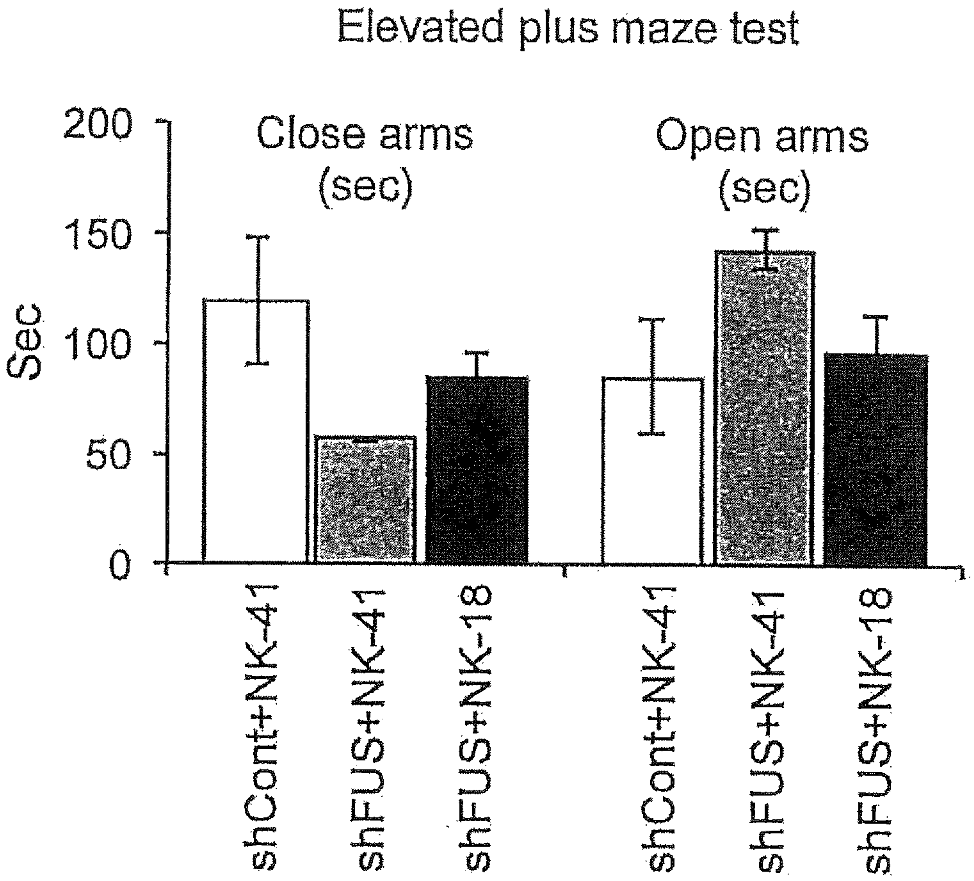
Figures 2, 13:
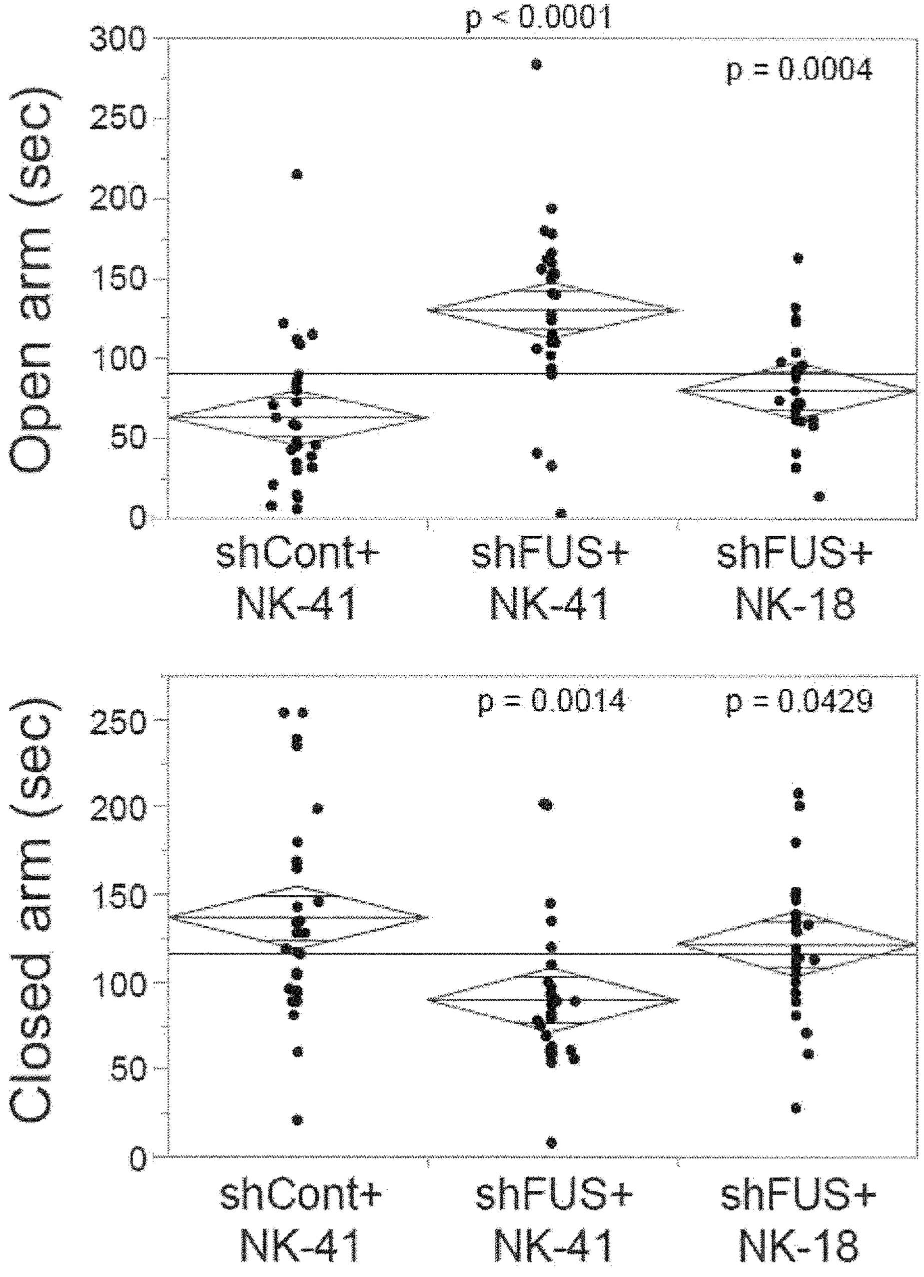

(1) Four weeks after administration of control AAV-shRNA (shCont) or AAV-shFUS to the both sides of hippocampus of hT-PAC-N mice, ASO was administered by intraventricular bolus administration. The abnormal emotional behavior was analyzed by the elevated plus maze test. The results are shown in FIG. 13-1.

shFUS prolongs the staying time in open arm (shFUS+NK-41, n=3); however, NK-18 administration shortened the staying time (shFUS+NK-18, n=4).

(2) An experiment similar to that in (1) was performed in many cases (total of the number of mice measured in (1) and the number of mice measured in the additional experiment, shCont+NK-41: n=28 each, shFUS+NK-41: n=27 each, shFUS+NK-18, n=26 each). The results are shown in FIG. 13-2.

In the same manner as described above, shFUS prolongs the staying time in open arm (shFUS+NK-41); however, NK-18 administration shortened the staying time (shFUS+NK-18). Conversely, shFUS shortened the staying time in closed arm (shFUS+NK-41); however, NK-18 administration prolonged the staying time (shFUS+NK-18).

Example 10 Effect of Promoting ASO Using Motor Neuron with FUS Knockdown

Figure 14:
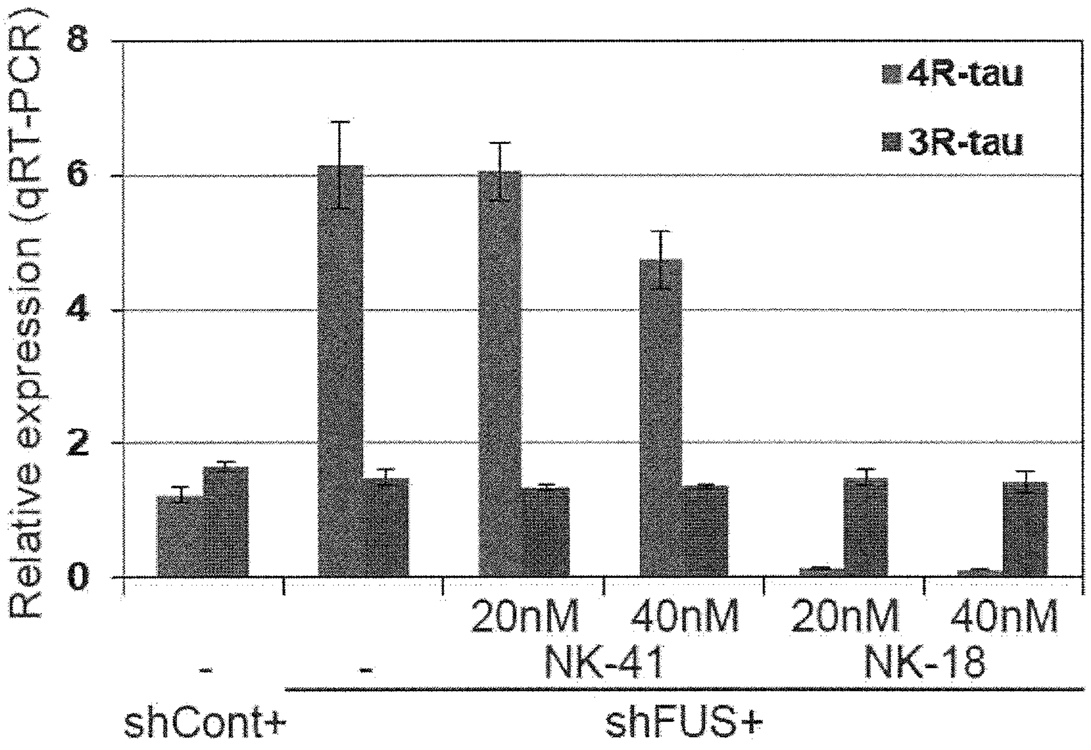
FIG. 14 shows the endogenous tau exon 10 skipping effect of an ENA-modified ASO (NK-18) in human iPS cell-derived differentiated motor neuron (under FUS KD). shCont indicates control AAV-shRNA, and NK-41 indicates control ASO.

Differentiation of human iPS cells into motor neurons was induced according to the method described in the previous report (Mol Brain. 2015; 8:79.). Four weeks after simultaneous administration of AAV-shFUS and 20 nM or 40 nM ASO, RNA was extracted, and 4R-tau and 3R-tau mRNAs were measured by qRT-PCR (n=3). The results are shown in FIG. 14. AAV-shFUS increased 4R-tau mRNA expression, and NK-18 (20 nM and 40 nM) markedly decreased the mRNA expression level thereof. shCont indicates control AAV-shRNA, and NK-41 indicates control ASO.

INDUSTRIAL APPLICABILITY

The ASO of the present invention concurrently has a high tau splicing regulating potency and long-term in vivo stability, and has also been confirmed to have tolerability by intraventricular administration to mice. Therefore, it is expected to exhibit a superior treatment effect on tauopathy with a low dose and low administration frequency. Therefore, the ASO of the present invention not only provides a novel therapeutic approach to tauopathy, for which an effective treatment method has never existed, but also places less burden of administration, is minimally invasive, can suppress manifestation of adverse events, and is useful for improving the QOL of patients. Furthermore, it also leads to the reduction of production cost (medical expenses).

Using the ASO of the present invention, the 4R/3R-tau expression ratio can be highly controlled. Therefore, it is applicable to the production of cultured cells and animal tauopathy models, and highly useful for elucidation of the pathology of tauopathy and screening for a therapeutic and/or prophylactic drug.

This application is based on a patent application No. 2018-127872 filed in Japan (filing date: Jul. 4, 2018), the contents of which are incorporated in full herein.

The invention claimed is:

1. A tau exon 10 skipping-promoting antisense oligonucleotide consisting of a sequence selected from the group consisting of SEQ ID NOs: 2, 5, 12, 16, 18, 20, and 21, wherein thymine may be uracil, wherein all pyrimidine nucleotides in the antisense oligonucleotide are 2'-O, 4'-C-ethylene-bridged nucleic acids, and all purine nucleotides in the antisense oligonucleotide are 2'O-methyl-modified nucleic acids, and wherein all phosphodiester bonds are phosphorothioated.

2. The antisense oligonucleotide according to claim 1, wherein the antisense oligonucleotide consists of the sequence of SEQ ID NO: 18.

3. A tau exon 10 skipping-promoting method, comprising introducing an effective amount of the antisense oligonucleotide according to claim 1 into a subject.

4. A method for treating tauopathy associated with accumulation of 4R-tau in a mammal in need thereof, comprising administering an effective amount of the antisense oligonucleotide according to claim 1 to the mammal.

5. The method according to claim 4, wherein the tauopathy is frontotemporal dementia, frontotemporal lobar degeneration, corticobasal degeneration, progressive supranuclear palsy, Alzheimer's disease, senile dementia of the neurofibrillary tangle type, chronic traumatic encephalopathy or argyrophilic grain dementia.

* * * * *

SEQUENCE LISTING

```
<160> NUMBER OF SEQ ID NOS: 80

<210> SEQ ID NO 1
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau intron 9

<400> SEQUENCE: 1

agccagaaaa aaggatga                                                 18


<210> SEQ ID NO 2
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau exon 10

<400> SEQUENCE: 2

tggacgttgc taagatcc                                                 18


<210> SEQ ID NO 3
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau exon 10
```

-continued

<400> SEQUENCE: 3
cacacttgga ctggacgt 18

<210> SEQ ID NO 4
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 4
ccacacttgg actggacg 18

<210> SEQ ID NO 5
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 5
gccacacttg gactggac 18

<210> SEQ ID NO 6
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 6
agccacactt ggactgga 18

<210> SEQ ID NO 7
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 7
gagccacact tggactgg 18

<210> SEQ ID NO 8
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 8
tgagccacac ttggactg 18

<210> SEQ ID NO 9
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 9
ttgagccaca cttggact 18

<210> SEQ ID NO 10
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 10
tttgagccac acttggac 18

<210> SEQ ID NO 11
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 11
ctttgagcca cacttgga 18

<210> SEQ ID NO 12
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 12
cctttgagcc acacttgg 18

<210> SEQ ID NO 13
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 13
tcctttgagc cacacttg 18

<210> SEQ ID NO 14
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 14
atcctttgag ccacactt 18

<210> SEQ ID NO 15
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 15

-continued

```
tatcctttga gccacact                                                   18


<210> SEQ ID NO 16
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau exon 10

<400> SEQUENCE: 16

ttatcctttg agccacac                                                   18


<210> SEQ ID NO 17
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau exon 10

<400> SEQUENCE: 17

attatccttt gagccaca                                                   18


<210> SEQ ID NO 18
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau exon 10

<400> SEQUENCE: 18

tattatcctt tgagccac                                                   18


<210> SEQ ID NO 19
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau exon 10

<400> SEQUENCE: 19

atattatcct ttgagcca                                                   18


<210> SEQ ID NO 20
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau exon 10

<400> SEQUENCE: 20

gatattatcc tttgagcc                                                   18


<210> SEQ ID NO 21
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau exon 10

<400> SEQUENCE: 21
```

ggacgtgttt gatattat 18

<210> SEQ ID NO 22
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 22
gcatgggacg tgtgaagg 18

<210> SEQ ID NO 23
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 23
ggcgcatggg acgtgtga 18

<210> SEQ ID NO 24
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 24
gcacggcgca tgggacgt 18

<210> SEQ ID NO 25
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 25
tttattctat gcagtgtc 18

<210> SEQ ID NO 26
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 26
gcccaagaag gatttatt 18

<210> SEQ ID NO 27
<211> LENGTH: 19
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 27
tggacgttgc taagatcca 19

-continued

<210> SEQ ID NO 28
<211> LENGTH: 19
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 28
ctggacgttg ctaagatcc 19

<210> SEQ ID NO 29
<211> LENGTH: 19
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 29
gccacacttg gactggacg 19

<210> SEQ ID NO 30
<211> LENGTH: 19
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 30
agccacactt ggactggac 19

<210> SEQ ID NO 31
<211> LENGTH: 19
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 31
tattatcctt tgagccaca 19

<210> SEQ ID NO 32
<211> LENGTH: 19
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 32
ggacgtgtga aggtactca 19

<210> SEQ ID NO 33
<211> LENGTH: 19
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 33
gggacgtgtg aaggtactc 19

-continued

<210> SEQ ID NO 34
<211> LENGTH: 17
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 34
ggacgttgct aagatcc 17

<210> SEQ ID NO 35
<211> LENGTH: 17
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 35
tggacgttgc taagatc 17

<210> SEQ ID NO 36
<211> LENGTH: 17
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 36
ccacacttgg actggac 17

<210> SEQ ID NO 37
<211> LENGTH: 17
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 37
gccacacttg gactgga 17

<210> SEQ ID NO 38
<211> LENGTH: 17
<212> TYPE: DNA
<213> ORGANISM: Artificial Sequence
<220> FEATURE:
<223> OTHER INFORMATION: Synthetic sequence, antisense oligonucleotide
targeting Tau intron 10

<400> SEQUENCE: 38
gacgtgtgaa ggtactc 17

<210> SEQ ID NO 39
<211> LENGTH: 17
<212> TYPE: DNA
<213> ORGANISM: Artificial Sequence
<220> FEATURE:
<223> OTHER INFORMATION: Synthetic sequence, antisense oligonucleotide
targeting Tau intron 10

<400> SEQUENCE: 39
ggacgtgtga aggtact 17

-continued

<210> SEQ ID NO 40
<211> LENGTH: 18
<212> TYPE: DNA
<213> ORGANISM: Artificial Sequence
<220> FEATURE:
<223> OTHER INFORMATION: Synthetic sequence, control antisense oligonucleotide

<400> SEQUENCE: 40
catctaagca acaattga 18

<210> SEQ ID NO 41
<211> LENGTH: 18
<212> TYPE: DNA
<213> ORGANISM: Artificial Sequence
<220> FEATURE:
<223> OTHER INFORMATION: Synthetic sequence, control antisense oligonucleotide

<400> SEQUENCE: 41
ctcttgacgc acatctgg 18

<210> SEQ ID NO 42
<211> LENGTH: 18
<212> TYPE: DNA
<213> ORGANISM: Artificial Sequence
<220> FEATURE:
<223> OTHER INFORMATION: Synthetic sequence, control antisense oligonucleotide

<400> SEQUENCE: 42
ttccctgaag gttcctcc 18

<210> SEQ ID NO 43
<211> LENGTH: 18
<212> TYPE: DNA
<213> ORGANISM: Artificial Sequence
<220> FEATURE:
<223> OTHER INFORMATION: Synthetic sequence, control antisense oligonucleotide

<400> SEQUENCE: 43
tcagtaaact tgacacca 18

<210> SEQ ID NO 44
<211> LENGTH: 40
<212> TYPE: DNA
<213> ORGANISM: Homo sapiens

<400> SEQUENCE: 44
gcaacgtcca gtccaagtgt ggctcaaagg ataatatcaa 40

<210> SEQ ID NO 45
<211> LENGTH: 31
<212> TYPE: DNA
<213> ORGANISM: Homo sapiens

<400> SEQUENCE: 45
tgagtacctt cacacgtccc atgcgccgtg c 31

<210> SEQ ID NO 46
<211> LENGTH: 234
<212> TYPE: DNA
<213> ORGANISM: Homo sapiens

<400> SEQUENCE: 46

-continued tgtcactcat cctttttct ggctaccaaa ggtgcagata attaataaga agctggatct 60
tagcaacgtc cagtccaagt gtggctcaaa ggataatatc aaacacgtcc cgggaggcgg 120
cagtgtgagt accttcacac gtcccatgcg ccgtgctgtg gcttgaatta ttaggaagtg 180
gtgtgagtgc gtacacttgc gagacactgc atagaataaa tccttcttgg gctc 234

<210> SEQ ID NO 47
<211> LENGTH: 35
<212> TYPE: DNA
<213> ORGANISM: Homo sapiens

<400> SEQUENCE: 47
acgtccagtc caagtgtggc tcaaaggata atatc 35

<210> SEQ ID NO 48
<211> LENGTH: 21
<212> TYPE: DNA
<213> ORGANISM: Homo sapiens

<400> SEQUENCE: 48
ccttcacacg tcccatgcgc c 21

<210> SEQ ID NO 49
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 49
gacgtgtttg atattatc 18

<210> SEQ ID NO 50
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 50
acgtgtttga tattatcc 18

<210> SEQ ID NO 51
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 51
cgtgtttgat attatcct 18

<210> SEQ ID NO 52
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 52
gtgtttgata ttatcctt 18

<210> SEQ ID NO 53
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 53
tgtttgatat tatccttt 18

<210> SEQ ID NO 54
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 54
gtttgatatt atcctttg 18

<210> SEQ ID NO 55
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 55
tttgatatta tcctttga 18

<210> SEQ ID NO 56
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 56
ttgatattat cctttgag 18

<210> SEQ ID NO 57
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 57
tgatattatc ctttgagc 18

<210> SEQ ID NO 58
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau exon 10

<400> SEQUENCE: 58
acacttggac tggacgtt 18

<210> SEQ ID NO 59
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 59
cacttggact ggacgttg 18

<210> SEQ ID NO 60
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 60
acttggactg gacgttgc 18

<210> SEQ ID NO 61
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 61
cttggactgg acgttgct 18

<210> SEQ ID NO 62
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 62
ttggactgga cgttgcta 18

<210> SEQ ID NO 63
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 63
tggactggac gttgctaa 18

<210> SEQ ID NO 64
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 64
ggactggacg ttgctaag 18

-continued

<210> SEQ ID NO 65
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 65
gactggacgt tgctaaga 18

<210> SEQ ID NO 66
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 66
actggacgtt gctaagat 18

<210> SEQ ID NO 67
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau exon 10

<400> SEQUENCE: 67
ctggacgttg ctaagatc 18

<210> SEQ ID NO 68
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 68
cacggcgcat gggacgtg 18

<210> SEQ ID NO 69
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 69
acggcgcatg ggacgtgt 18

<210> SEQ ID NO 70
<211> LENGTH: 18
<212> TYPE: DNA
<213> ORGANISM: Artificial Sequence
<220> FEATURE:
<223> OTHER INFORMATION: Synthetic sequence, antisense oligonucleotide targeting Tau intron 10

<400> SEQUENCE: 70
cggcgcatgg gacgtgtg 18

<210> SEQ ID NO 71

<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau intron 10

<400> SEQUENCE: 71
gcgcatggga cgtgtgaa 18

<210> SEQ ID NO 72
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau intron 10

<400> SEQUENCE: 72
cgcatgggac gtgtgaag 18

<210> SEQ ID NO 73
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau intron 10

<400> SEQUENCE: 73
catgggacgt gtgaaggt 18

<210> SEQ ID NO 74
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau intron 10

<400> SEQUENCE: 74
atgggacgtg tgaaggta 18

<210> SEQ ID NO 75
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau intron 10

<400> SEQUENCE: 75
tgggacgtgt gaaggtac 18

<210> SEQ ID NO 76
<211> LENGTH: 18
<212> TYPE: DNA
<213> ORGANISM: Artificial Sequence
<220> FEATURE:
<223> OTHER INFORMATION: Synthetic sequence, antisense oligonucleotide
targeting Tau intron 10

<400> SEQUENCE: 76
gggacgtgtg aaggtact 18

<210> SEQ ID NO 77
<211> LENGTH: 18

-continued

```
<212> TYPE: DNA
<213> ORGANISM: Artificial Sequence
<220> FEATURE:
<223> OTHER INFORMATION: Synthetic sequence, antisense oligonucleotide
      targeting Tau intron 10

<400> SEQUENCE: 77

ggacgtgtga aggtactc                                                18


<210> SEQ ID NO 78
<211> LENGTH: 18
<212> TYPE: DNA
<213> ORGANISM: Artificial Sequence
<220> FEATURE:
<223> OTHER INFORMATION: Synthetic sequence, antisense oligonucleotide
      targeting Tau intron 10

<400> SEQUENCE: 78

gacgtgtgaa ggtactca                                                18


<210> SEQ ID NO 79
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 79

ccatgccaga cctgaagaat                                              20


<210> SEQ ID NO 80
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 80

tgctcaggtc aactggtttg                                              20
```